(12) United States Patent
Koyama et al.

(10) Patent No.: US 8,513,289 B2
(45) Date of Patent: Aug. 20, 2013

(54) P38 KINASE INHIBITING AGENTS

(75) Inventors: Hiroo Koyama, Hoboken, NJ (US); Soumya P. Sahoo, Old Bridge, NJ (US); Ginger Xu-Qiang Yang, Jersey City, NJ (US); Daniel J. Miller, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 4 days.

(21) Appl. No.: 13/266,043

(22) PCT Filed: Apr. 26, 2010

(86) PCT No.: PCT/US2010/032345
§ 371 (c)(1),
(2), (4) Date: Oct. 24, 2011

(87) PCT Pub. No.: WO2010/129208
PCT Pub. Date: Nov. 11, 2010

(65) Prior Publication Data
US 2012/0040999 A1    Feb. 16, 2012

Related U.S. Application Data

(60) Provisional application No. 61/223,312, filed on Aug. 12, 2009, provisional application No. 61/175,474, filed on May 5, 2009.

(51) Int. Cl.
| | | |
|---|---|---|
| *A61K 31/4245* | (2006.01) | |
| *A61K 31/433* | (2006.01) | |
| *C07D 285/08* | (2006.01) | |
| *C07D 207/333* | (2006.01) | |

(52) U.S. Cl.
USPC .......................... 514/361; 548/128; 548/518

(58) Field of Classification Search
USPC .................................. 514/361; 548/128, 131
See application file for complete search history.

(56) References Cited

U.S. PATENT DOCUMENTS
2004/0077707 A1    4/2004    Desai et al.
2007/0149594 A1    6/2007    Finsinger et al.

FOREIGN PATENT DOCUMENTS
WO    2009015208    *    1/2009

OTHER PUBLICATIONS

How Can Asthma Be Prevented, http://www.nhlbi.nih.gov/health/health-topics/topics/asthma/prevention.html, accessed Dec. 18, 2012.*
Mayer et al, 2006, Drug Discovery Today: Therapeutic Strategies, vol. 3, No. 1, p. 49-54.*
Goldstein, J. Med. Chem., 2010, vol. 53, p. 2345-2353.*

* cited by examiner

*Primary Examiner* — Wu-Cheng Winston Shen
*Assistant Examiner* — Karen Cheng
(74) *Attorney, Agent, or Firm* — Maria V. Marucci

(57) ABSTRACT

Compounds described by the chemical formula (I) or pharmaceutically acceptable salts thereof: Formula (I); are inhibitors of p38 and are useful in the treatment of inflammation such as in the treatment of asthma, COPD, ARDS, rheumatoid arthritis, rheumatoid spondylitis, osteoarthritis, gouty arthritis and other arthritic conditions; inflamed joints, eczema, psoriasis or other inflammatory skin conditions such as sunburn; inflammatory eye conditions including conjunctivitis; pyresis, pain and other conditions associated with inflammation.

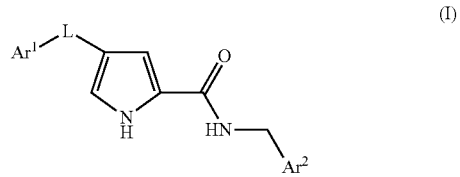

(I)

16 Claims, No Drawings

P38 KINASE INHIBITING AGENTS

CROSS REFERENCE TO RELATED APPLICATIONS

This application is a U.S. National Phase application under 35 U.S.C. §371 of PCT Application No. PCT/US2010/032345, filed Apr. 26, 2010, which claims the benefit under 35 U.S.C. §119(e) from U.S. Provisional Application Serial No. 61/175,474, filed May 5, 2009 and U.S. Provisional Application Serial No. 61/233,312, filed Aug. 12, 2009.

BACKGROUND OF THE INVENTION

The present invention relates to heterobicyclic compounds that inhibit the action of the p38 mitogen-activated protein kinase, a mammalian protein kinase that is involved in cell proliferation, cell response to stimuli, and cell death. In particular, this invention relates to heterobicyclic compounds that are selective and potent inhibitors of the p38 mitogen-activated protein kinase. This invention also relates to pharmaceutical compositions containing such heterobicyclic compounds that inhibit the p38 mitogen-activated protein kinase.

RELATED BACKGROUND

The Mitogen-Activated Protein (MAP) kinases are a family of proline-directed serine/threonine kinases that are activated by dual phosphorylation, and in turn phosphorylate their substrates on either Threonine-Proline or Serine-Proline sites.

MAP kinases are activated in response to a variety of signals including nutritional and osmotic stress, W light, growth factors, endotoxin and inflammatory cytokines. The p38 sub-group of MAP kinases (p38, also known as CSBP and RK) is a MAP kinase family of various isoforms, which is responsible for phosphorylating a large number of substrates, including transcription factors (e.g. ATF2, CHOP and MEF2C), other kinases (e.g. MAPKAP-2 and MAPKAP-3), tumor suppressors (e.g. p53) and translational regulators (e.g. 3EBP, PRAK).

A large number of chronic and acute conditions have been recognized to be associated with perturbation of the inflammatory response. A large number of cytokines participate in this response, including IL-1, IL-6, IL-8 and TNF. It appears that the expression, secretion and activity of these cytokines in the regulation of inflammation rely at least in part on the activation of p38. This kinase is activated by dual phosphorylation after stimulation by physiochemical stress, treatment with lipopolysaccharides or with pro-inflammatory cytokines such as IL-1, and TNF.

TNF and interleukins such as IL-1 and IL-8 affect a wide variety of cells and tissues and are important inflammatory mediators of a wide variety of disease states and conditions. TNF-α is a cytokine produced primarily by activated monocytes and macrophages. Excessive or unregulated TNF production has been implicated in mediating a number of diseases. Recent studies indicate that TNF has a causative role in the pathogenesis of rheumatoid arthritis. Additional studies demonstrate that inhibition of TNF has broad application in the treatment of inflammation, inflammatory bowel disease, multiple sclerosis and asthma. TNF has also been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein-Barr virus, human herpesvirus-6 (HHV-6), human herpesvirus-7 (HHV-7), human herpesvirus-8 (HHV-8), pseudorabies and rhinotracheitia, among others. IIL-8 is another pro-inflammatory cytokine, which is produced by mononuclear cells, fibroblasts, endothelial cells, and keratinocytes, and is associated with pathological conditions including inflammation.

IL-1 is produced by activated monocytes and macrophages and is involved in the inflammatory response. IL-1 plays a role in many pathophysiological responses including rheumatoid arthritis, fever and reduction of bone resorption.

TNF, IL-1 and IL-8 affect a wide variety of cells and tissues and are important inflammatory mediators of a wide variety of disease states and conditions. The inhibition of these cytokines by inhibition of the p38 kinase is of benefit in controlling, reducing and alleviating many of these disease states.

Within the past several years, p38 has been shown to comprise a group of MAP I kinases designated p38δ, p38γ, p38β, p38α, Jiang, Y., et al., (A Biol Chem I (1996) 271:17920-17926) reported characterization of p38β as a 372-amino acid protein closely related to p38-α. In comparing the activity of p38α with that of p38β, the authors state that while both are activated by proinflammatory cytokines and environmental stress, p38β was preferentially activated by MAP kinase kinase-6 (MKK6) and preferentially activated transcription factor 2, thus suggesting that separate mechanisms for action may be associated with these forms. Kumar, S., et al., (Biochem Biophys Res Comm (1997) 235:533-538) and Stein, B., et al., (J Biol Chem (1997) 272: 19509-19517) reported a second isoform of p38β-p38β2, containing 364 amino acids with 73% identity to p38α. All of these reports show evidence that p38β is activated by proinflammatory cytokines and environmental stress, although the second reported p38β isoform—p38β2, appears to be preferentially expressed in the CNS, heart and skeletal muscle compared to the more ubiquitous tissue expression of p38α. Furthermore, activated transcription factor-2 (ATF-2) was observed to be a better substrate for p38β2 than for p38αthus suggesting that separate mechanisms of action may be associated with these forms. The physiological role of p38β1 has been called into question by the latter two reports since it cannot be found in human tissue and does not exhibit appreciable kinase activity with the substrates of p38α.

The identification of p38γ was reported by Li, Z., et al., (Biochem Biophys Res Comm (1996) 228:334-340) and of p38δ by Wang, X., et al., (J Biol Chem (1997) 272:23668-23674) and by Kumar, S., et al., (Biochem Biophys Res Comm (1997) 235:533-538). The data suggest that these two p38 isoforms (γ and δ) represent a unique subset of the MAPK family based on their tissue expression patterns, substrate utilization, response to direct and indirect stimuli, and susceptibility to kinase inhibitors. Various results with regard to differential response to drugs targeting the p38 family as between p38α and either the putative p38β1 or p38β2, or both were reported by Jiang, Kumar, and Stein cited above as well as by Eyers, P. A., et al., (Chem and Biol (1995) 5:321-328). An additional paper by Wang, Y., et al., (J Biol Chem (1998) 273:2161-2168) suggests the significance of such differential effects. As pointed out by Wang et al., a number of stimuli, such as myocardial infarction, hypertension, valvular diseases, viral myocarditis, and dilated cardiomyopathy lead to an increase in cardiac workload and elevated mechanical stress on cardiomyocytes.

These are said to lead to an adaptive hypertrophic response, which, if not controlled, has decidedly negative consequences. Wang et al. cite previous studies which have shown that in ischemia reperfusion treated hearts, p38 MAPK activities are elevated in association with hypertrophy and programmed cell death. Wang et al. show in the cited paper that activation of p38β activity results in hypertrophy, whereas activation of p38α activity leads to myocyte apoptosis.

Thus, selective inhibition of p38α activity as compared to p38β activity will be of benefit in treating conditions associated with cardiac failure. These conditions I include congestive heart failure, cardiomyopathy, myocarditis, vasculitis, vascular restenosis, valvular disease, conditions associated with cardiopulmonary bypass, coronary artery bypass, grafts and vascular grafts. Further, to the extent that the α-isoform is toxic in other muscle cell types, α-selective inhibitors would be useful for conditions associated with cachexia attributed to TNF or other conditions such as cancer, infection, or autoimmune disease.

PCT applications W 098/06715, W 098/07425, W 098/28292 and WO 96/40143, describe the relationship of p38 kinase inhibitors with various disease states. As mentioned in these applications, inhibitors of p38 kinase are useful in treating a variety of diseases associated with chronic inflammation. These applications list rheumatoid arthritis, rheumatoid spondylitis, osteoarthritis, gouty arthritis and other arthritic conditions, sepsis, septic shock, endotoxic shock, Gram-negative sepsis, toxic shock syndrome, asthma, adult respiratory distress syndrome, stroke, reperfusion injury, CNS injuries such as neural trauma and ischemia, psoriasis, restenosis, cerebral I malaria, chronic pulmonary inflammatory disease, silicosis, pulmonary sarcosis, bone resorption diseases such as osteoporosis, graft-versus-host reaction, Crohn's Disease, ulcerative colitis including inflammatory bowel disease (IBD) and pyresis.

SUMMARY OF THE INVENTION

Compounds described by the chemical formula (A) or pharmaceutically acceptable salts thereof:

(A)

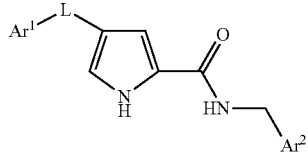

are inhibitors of p38 and are useful in the treatment of inflammation such as in the treatment of asthma, COPD, ARDS, rheumatoid arthritis, rheumatoid spondylitis, osteoarthritis, gouty arthritis and other arthritic conditions; inflamed joints, eczema, psoriasis or other inflammatory skin conditions such as sunburn; inflammatory eye conditions including conjunctivitis; pyresis, pain and other conditions associated with inflammation.

DETAILED DESCRIPTION OF THE INVENTION

In one embodiment, the present invention provides p38 inhibitor compounds of the chemical formula (A):

(I)

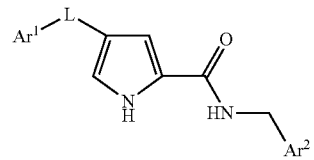

or a pharmaceutically acceptable salt thereof, wherein:
L is selected from the group consisting of:
  (a) —C(O)—,
  (b) —CH(OH)—,
  (c) —CH($NR^3R^4$)—,
  (d) —C(=$NOR^3$)—,
  (e) —$CH_2$—, and
  (f) —S(O)$_n$—, wherein n is 0, 1 or 2;
$Ar^1$ is an optionally mono, di- or tri-substituted phenyl or heteroaromatic ring of 6 atoms, wherein the heteroaromatic ring may contain 1, 2 or 3 heteroatoms selected from N, S and O, wherein the substituents are independently selected from the group consisting of:
  (a) halo,
  (b) —$C_{1-4}$alkyl,
  (c) —O—$C_{1-4}$alkyl,
  (d) —$CF_3$,
  (e) —$NH_2$,
  (f) —NH—$CH_3$,
  (g) —CN,
  (h) —C(O)$NH_2$, and
  (i) —S(O)$_n$—$CH_3$;
$Ar^2$ is an optionally substituted thiadiazole or oxadiazole ring wherein the substituent is q phenyl or a 5 or 6 membered mono-cyclic heteroaromatic or heterocyclic ring, or a bicyclic heteroaromatic or heterocyclic ring of 9 or 10 atoms, said heteroaromatic or heterocyclic ring containing 1, 2 or 3 hetero atoms selected from the group consisting of S, O and N, where in said phenyl, heteroaromatic or heterocyclic ring is optionally mono or di-substituted with substituents independently selected from the group consisting of:
  (a) halo,
  (b) —$C_{1-6}$alkyl, optionally substituted with 1 to 4 fluorine atoms
  (c) —O—$C_{1-6}$alkyl,
  (d) —$CF_3$,
  (e) —$NH_2$, and
  (f) —$NH_2$—$CH_3$,
  (g) $NH_2$—$CH_2CF_3$,
  (h) —C(O)-morpholinyl,
  (i) —C(O)—$NR^1R^2$,
  (j) —C(O)OH,
  (k) —CN,
  (l) oxo, and
  (m) $C_{3-6}$cycloalkyl;
$R^1$, $R^2$, $R^3$ and $R^4$ are independently selected from the group consisting of
  (a) hydrogen, and
  (b) $C_{1-4}$alkyl,
or $R^1$ and $R^2$ or $R^3$ and $R^4$ may be joined together to form a 5 or 6 membered saturated ring, said ring optionally containing a heteroatom selected from S, N and O.
Within this embodiment there is a genus wherein
L is selected from the group consisting of:
  (a) —C(O)—, and
  (b) —$CH_2$—.
Within this genus there is a sub-genus wherein
L is —C(O)—.
Within this embodiment where is a genus wherein
$Ar^1$ is an optionally mono, di- or tri-substituted phenyl or heteroaromatic ring of 6 atoms, wherein the heteroaromatic ring may contain 1, 2 or 3 heteroatoms selected from N, S and O, wherein the substituents are independently selected from the group consisting of
  (a) halo,
  (b) —$C_{1-4}$alkyl, and
  (c) —O—$C_{1-4}$alkyl.
Within this genus there is a sub-genus wherein
$Ar^1$ is an optionally mono, di- or tri-substituted phenyl or pyridyl, wherein the substituents are independently selected from the group consisting of (a) fluoro,
(b) chloro, and
(c) —CH$_3$.

Within this sub-genus there is a class wherein
Ar$^1$ is an optionally mono, di- or tri-substituted phenyl, wherein the substituents are independently selected from the group consisting of
(a) fluoro,
(b) chloro, and
(c) —CH$_3$.

Within this embodiment there is a genus wherein
Ar$^2$ is an optionally substituted thiadiazolyl.

Within this genus there is a sub-genus wherein the substituent is phenyl or a 5 or 6 membered mono-cyclic heteroaromatic or heterocyclic ring, or a 9 or 10 atom bicyclic heteroaromatic or heterocyclic ring, said hetero aromatic or heterocyclic ring containing 1, 2 or 3 hetero atoms selected from the group consisting of S, O and N, where in said phenyl, heteroaromatic or heterocyclic ring is optionally mono or di-substituted with substituents independently selected from the group consisting of:
(a) halo,
(b) —C$_{1-6}$alkyl, optionally substituted with CF$_3$,
(c) —O—C$_{1-4}$alkyl,
(d) —CF$_3$, and
(e) C$_{3-6}$cycloalkyl.

Within this sub-genus there is a class wherein the substituent is phenyl or a 5 or 6 membered mono-cyclic heteroaromatic or heterocyclic ring, said hetero aromatic or heterocyclic ring containing 1, 2 or 3 hetero atoms selected from the group consisting of S, O and N, where in said phenyl, heteroaromatic or heterocyclic ring is optionally mono or di-substituted with substituents independently selected from the group consisting of:
(a) halo,
(b) —C$_{1-6}$alkyl, optionally substituted with CF$_3$,
(c) —O—C$_{1-4}$alkyl,
(d) —CF$_3$, and
(e) C$_{3-6}$cycloalkyl.

Within this embodiment there is a genus wherein
R$^1$, R$^2$, R$^3$ and R$^4$ are independently selected from the group consisting of
(a) hydrogen, and
(b) methyl.

Within this embodiment there is a genus of Formula I (I)

or a pharmaceutically acceptable salt thereof, wherein:
L is —C(O)—;
Ar$^1$ is an optionally mono, di- or tri-substituted phenyl, wherein the phenyl, wherein the substituents are independently selected from the group consisting of:
(a) F,
(b) Cl,
(c) —C$_{1-4}$alkyl, and
(d) —O—C$_{1-4}$alkyl;

Ar$^2$ is optionally substituted thiadiazolyl, and the substituent is phenyl or a 5 or 6 membered mono-cyclic heteroaromatic or heterocyclic ring, said hetero aromatic or heterocyclic ring containing 1, 2 or 3 hetero atoms selected from the group consisting of S, O and N, where in said phenyl, heteroaromatic or heterocyclic ring is optionally mono or di-substituted with substituents independently selected from the group consisting of:
(a) halo,
(b) —C$_{1-4}$alkyl,
(c) —O—C$_{1-4}$alkyl,
(d) —CF$_3$,
(e) C$_{3-6}$cycloalkyl.

Within this genus there is a sub-genus of Formula II (II)

or a pharmaceutically acceptable salt thereof, wherein:
Ar$^2$ is optionally substituted thiadiazolyl, wherein the substituent is phenyl or a 5 or 6 membered mono-cyclic heteroaromatic or heterocyclic ring, said hetero aromatic or heterocyclic ring containing 1, 2 or 3 hetero atoms selected from the group consisting of S, O and N, where in said phenyl, heteroaromatic or heterocyclic ring is optionally mono or di-substituted with substituents independently selected from the group consisting of:
(a) halo,
(b) —C$_{2-6}$alkyl,
(c) —O—C$_{1-4}$alkyl, and
(d) —CF$_3$.

As discussed above, the p38 sub-group of MAP kinases is a MAP kinase family of various isoforms (including p38δ, p38γ, p38β, p38α), which is responsible for phosphorylating a large number of downstream substrates. Data suggests that two p38 isoforms (α and β) represent a unique subset of the MAPK family based on their tissue expression patterns, substrate utilization, response to direct and indirect stimuli, and susceptibility to kinase inhibitors. Various results with regard to differential response to drugs targeting the p38 family as between p38-α and either the putative p38-β1 or p38-β2, or both were reported by Jiang, Kumar, and Stein supra, as well as by Eyers, P. A., et al., [Chem and Biol (1995) 5:321-328]. An additional paper by Wang, Y., et al., [J Biol Chem (1998) 273:2161-2168] suggests the significance of such differential effects of selectively inhibiting p38-α. Canonical inhibitors of p38-α inhibit phosphorylation of downstream substrates, including, but not limited to, MK2, MK3, ATF2, Mnk2a, MSK1, TAB1, CREB and HSP27. Based on these data, p38-α inhibitors that preferentially inhibit phosphorylation of one subset of these downstream substrates should exhibit an increased therapeutic index relative to canonical p38 inhibitors.

In a still further aspect, the invention is directed to compounds of Formula I which are potent inhibits p38-α and selectively inhibit phosphorylation of one or more of MK2, MK3, ATF2, Mnk2a, MSK1 and TAB1, in preference to the rest of these or other downstream substrates. For example, in one aspect, the invention is direct to compounds of Formula I which selectively inhibit phosphorylation of MK2 and MK3 in preference to MSK1, ATF2 or a peptide substrate. Within this aspect are compounds of Formula I, which are potent inhibitors of p38-α and selectively inhibit phosphorylation of MK2 in preference to a peptide substrate as measured by an in vitro kinase assay.

The term "acetal" means a functional group or molecule containing a CH bonded to two —OR groups. A "cyclic acetal" thus means a cyclic or ring structure containing an acetal group.

The term "alkyl" means carbon chains that have no double or triple bonds, and that may be linear or branched or combinations thereof. Thus, $C_1$-$C_6$ alkyl is defined to identify the group as having 1, 2, 3, 4, 5 or 6 carbons in an arrangement that is linear, branched, or a combination thereof. Examples of alkyl groups include methyl, ethyl, propyl, n-propyl, iso-propyl, butyl, sec- and tert-butyl, pentyl, hexyl, heptyl and the like. The term "$C_0$-$C_4$alkyl" includes alkyls containing 4, 3, 2, 1, or no carbon atoms. An alkyl with no carbon atoms is a hydrogen atom substituent when the alkyl is a terminus moiety. An alkyl with no carbon atoms is a direct bond when the alkyl is a bridging moiety.

The term "alkene" means linear or branched structures and combinations thereof, of the indicated number of carbon atoms, having at least one carbon-to-carbon double bond, wherein hydrogen may be replaced by an additional carbon-to-carbon double bond. $C_2$-$C_6$ alkene, for example, includes ethylene, propylene, 1-methylethylene, butylene and the like.

The term "alkynyl" means linear or branched structures and combinations thereof, of the indicated number of carbon atoms, having at least one carbon-to-carbon triple bond. Thus $C_2$-$C_6$ alkynyl is defined to identify the group as having 2, 3, 4, 5 or 6 carbon in a linear or branched arrangement, such that $C_2$-$C_6$ alkynyl specifically includes 2-hexynyl and 2-pentynyl.

The term "alkoxy" as used herein, alone or in combination, includes an alkyl group connected to the oxy connecting atom. The term "alkoxy" also includes alkyl ether groups, where the term 'alkyl' is defined above, and 'ether' means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as 'dimethyl ether'), and methoxyethane (also referred to as 'ethyl methyl ether').

The term "amine" unless specifically stated otherwise includes primary, secondary and tertiary amines.

The term "aryl," unless specifically stated otherwise, is intended to mean any stable monocyclic or fused bicyclic carbon ring of up to 7 members in each ring, wherein at least one ring is aromatic. Examples of such aryl elements include phenyl, naphthyl and tolyl.

The term "aryloxy" unless specifically stated otherwise includes multiple ring systems as well as single ring systems such as, for example, phenyl or naphthyl, connected though the oxy connecting atom to the connecting site.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalenyl, adamantanyl, indanyl, indenyl, fluorenyl, 1,2,3,4-tetrahydronaphthalenyl and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "cycloalkyloxy" unless specifically stated otherwise includes a cycloalkyl group connected to the oxy connecting atom.

The term "hetero," unless specifically stated otherwise, includes one or more O, S, or N atoms. For example, heterocycloalkyl and heteroaryl include ring systems that contain one or more O, S, or N atoms in the ring, including mixtures of such atoms. The hetero atoms replace ring carbon atoms.

Examples of heterocycloalkyl include azetidinyl, pyrrolidinyl, piperidinyl, piperazinyl, morpholinyl, tetrahydrofuranyl, imidazolinyl, cyclic acetals, cyclic ketals, pyrrolidin-2-one, piperidin-2-one and thiomorpholinyl. As used herein, "heterocycloalkyl" includes bridged heterocycloalkyls having two or more heterocycloalkyl groups joined via adjacent or non-adjacent atoms.

The term "heteroaryl", as used herein except where noted, is intended to mean a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, pyridine, pyrimidine, pyrazine, thiophene, oxazole, thiazole, triazole, thiadiazole, oxadiazole, pyrrole, 1,2,4-oxadiazole, 1,3,4-oxadiazole, 1,2,4-thiadiazole, 1,3,4-thiadiazole, and 1,2,4-triazole.

Additional examples of heteroaryl include quinolinyl, pyrimidinyl, isoquinolinyl, pyridazinyl, quinoxalinyl, furyl, benzofuryl, dibenzofuryl, thienyl, benzothienyl, indolyl, indazolyl, isoxazolyl, isothiazolyl, imidazolyl, benzimidazolyl, thiadiazolyl, tetrazolyl.

The term "heteroaryloxy" unless specifically stated otherwise describes a heteroaryl group connected through an oxy connecting atom to the connecting site.

Examples of heteroaryl($C_{1-6}$)alkyl include, for example, furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

Unless otherwise stated, the term "carbamoyl" is used to include —NHC(O)OC1-C4alkyl, and —OC(O)NHC1-C4alkyl.

The term "halogen" includes fluorine, chlorine, bromine and iodine atoms.

The term "ketal" means a functional group or molecule containing a carbon bonded to two —OR groups. A "cyclic ketal" thus means a cyclic or ring structure containing a ketal group.

The term "optionally substituted" is intended to include both substituted and unsubstituted. Thus, for example, optionally substituted aryl could represent a pentafluorophenyl or a phenyl ring. Further, the substitution can be made at any of the groups. For example, substituted aryl($C_{1-6}$)alkyl includes substitution on the aryl group as well as substitution on the alkyl group.

The term "oxide" of heteroaryl groups is used in the ordinary well-known chemical sense and include, for example, N-oxides of nitrogen heteroatoms.

Compounds described herein contain one or more double bonds and may thus give rise to cis/trans isomers as well as other conformational isomers. The present invention includes all such possible isomers as well as mixtures of such isomers.

Unless specifically stated otherwise or indicated by a bond symbol (dash or double dash), the connecting point to a recited group will be on the right-most stated group. That is, for example, a phenylalkyl group is connected to the main structure through the alkyl and the phenyl is a substituent on the alkyl.

The compounds of the present invention are useful in various pharmaceutically acceptable salt forms. The term "pharmaceutically acceptable salt" refers to those salt forms which would be apparent to the pharmaceutical chemist. i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug. Conveniently, pharmaceutical compositions may be prepared from the active ingredients in combination with pharmaceutically acceptable carriers.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be mixtures of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized by conventional chemical methods. Generally, the salts are prepared by reacting the free base or acid with stoichiometric amounts or with an excess of the desired salt-forming inorganic or organic acid or base, in a suitable solvent or solvent combination.

The compounds of the present invention may have asymmetric centers and occur as racemates, racemic mixtures, and as individual diastereomers. All such isomers, including optical isomers, being included in the present invention.

The invention described herein also includes a pharmaceutical composition which is comprised of a compound described by Formula (I), or a pharmaceutically acceptable salt thereof, in combination with a pharmaceutically acceptable carrier.

The invention described herein also includes a pharmaceutical composition which is comprised of a compound described by Formula (I), or a pharmaceutically acceptable salt thereof, in combination with a pharmaceutically acceptable carrier. The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. Such additional therapeutic ingredients include, for example, i) Leukotriene receptor antagonists, ii) Leukotriene biosynthesis inhibitors, iii) corticosteroids, iv) H1 receptor antagonists, v) beta 2 adrenoceptor agonists, vi) COX-2 selective inhibitors, vii) statins, viii) non-steroidal anti-inflammatory drugs ("NSAID"), and ix) M2/M3 antagonists.

The invention described herein also includes a method of treating arthritis which is comprised of administering to a mammalian patient in need of such treatment a compound described by Formula (I), or a pharmaceutically acceptable salt thereof, in an amount which is effective to treat arthritis. The invention described herein also includes a method of treating arthritis which is comprised of administering to a mammalian patient in need of such treatment a compound described by Formula (I), or a pharmaceutically acceptable salt thereof, in an amount which is effective to treat arthritis. The invention includes methods of treating arthritis by administering to a mammalian patient in need of such treatment a compound described by Formula (I), or a pharmaceutically acceptable salt thereof, in combination or in coadministration with a COX-2 inhibitor.

The invention described herein also includes a method of treating a cytokine mediated disease in a mammal, comprising administering to a mammalian patient in need of such treatment an amount of a compound described by Formula (I), or a pharmaceutically acceptable salt thereof, in an amount which is effective to treat said cytokine mediated disease.

Of particular interest is a method of treating inflammation in a mammalian patient in need of such treatment, which is comprised of administering to said patient an anti-inflammatory effective amount of a compound described by Formula (I), or a pharmaceutically acceptable salt thereof.

Another method which is of particular interest is a method of treating a cytokine mediated disease as described herein wherein the disease is osteoporosis.

Another method which is of particular interest is a method of treating a cytokine mediated disease as described herein wherein the disease is non-osteoporotic bone resorption.

Yet another method which is of particular interest is a method of treating a cytokine mediated disease as described herein wherein the disease is Crohn's disease.

This invention also relates to a method of treating arthritis in a mammal in need such treatment, which comprises administering to said mammal an amount of a compound of formula I which is effective for treating arthritis. Such method includes the treatment of rheumatoid and osteoarthritis.

When administered to a patient for the treatment of arthritis, the dosage used can be varied depending upon the type of arthritis, the age and general condition of the patient, the particular compound administered, the presence or level of toxicity or adverse effects experienced with the drug, and other factors. A representative example of a suitable dosage range is from as low as about 0.01 mg/kg to as high as about 100 mg/kg. However, the dosage administered is generally left to the discretion of the physician.

This invention also relates to a method of inhibiting the action of p38 in a mammal in need thereof, which comprises administering to said mammal an effective amount of a compound described by Formula (I), or a pharmaceutically acceptable salt thereof, to inhibit said action of p38, down to normal levels, or in some cases to subnormal levels, so as to ameliorate, prevent or treat the disease state.

The compounds of formula I can be used in the prophylactic or therapeutic treatment of disease states in mammals which are exacerbated or caused by excessive or unregulated cytokines, more specifically IL-1, IL-6, IL-8 or TNF.

Because the compounds of formula I inhibit cytokines, such as IL-1, IL-6, IL-8 and TNF, by inhibiting the action of p38 the compounds are useful for treating diseases in which cytokine presence or activity is implicated, such as pain, rheumatoid arthritis, rheumatoid spondylitis, osteoarthritis, gouty arthritis and other arthritic conditions.

The compounds described by Formula (I, or a pharmaceutically acceptable salt thereof, are also useful to treat other disease states mediated by excessive or unregulated TNF production or activity. Such diseases include, but are not limited to sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, such as osteoporosis, reperfusion injury, graft v. host rejection, allograft rejection, fever, myalgia due to infection, cachexia secondary to infection or malignancy, cachexia secondary to acquired immune deficiency syndrome (AIDS), AIDS, ARC (AIDS related complex), keloid formation, scar tissue formation, Crohn's disease, ulcerative colitis, pyresis, AIDS and other viral infections, such as cytomegalovirus (CMV), influenza virus, and the herpes family of viruses such as Herpes Zoster or Simplex I and II.

The compounds described by Formula (I), or a pharmaceutically acceptable salt thereof, are also useful topically in the treatment of inflammation such as in the treatment of rheumatoid arthritis, rheumatoid spondylitis, osteoarthritis, gouty arthritis and other arthritic conditions; inflamed joints, eczema, psoriasis or other inflammatory skin conditions such as sunburn; inflammatory eye conditions including conjunctivitis; pyresis, pain and other conditions associated with inflammation.

The compounds described by Formula (I), or a pharmaceutically acceptable salt thereof, are also useful in treating diseases such as chronic obstructive pulmonary disease and diseases characterized by excessive IL-8 activity. These disease states include psoriasis, inflammatory bowel disease, asthma, cardiac and renal reperfusion injury, adult respiratory distress syndrome, thrombosis and glomerulonephritis.

The invention thus includes a method of treating psoriasis, inflammatory bowel disease, asthma, cardiac and renal reperfusion injury, adult respiratory distress syndrome, thrombosis and glomerulonephritis, in a mammal in need of such treatment, which comprises administering to said mammal a compound described by Formula (I), or a pharmaceutically acceptable salt thereof, in an amount which is effective for treating said disease or condition.

The compounds described by Formula (I), or a pharmaceutically acceptable salt thereof, are also useful for treating Alzheimer's disease. The instant invention thus includes a method of treating Alzheimer's disease in a mammal in need of such treatment, which comprises administering to said mammal a compound of Formula (I), or a pharmaceutically acceptable salt thereof, in an amount effective for treating said disease or condition.

When administered to a patient for the treatment of a disease in which a cytokine or cytokines are implicated, the dosage used can be varied depending upon the type of disease, the age and general condition of the patient, the particular compound administered, the presence or level of toxicity or adverse effects experienced with the drug, and other factors. A representative example of a suitable dosage range is from as low as about 0.01 mg/kg to as high as about 100 mg/kg. However, the dosage administered is generally left to the discretion of the physician.

The methods of treatment can be carried out by delivering the compound of formula I parenterally. The term 'parenteral' as used herein includes intravenous, intramuscular, or intraperitoneal administration. The subcutaneous and intramuscular forms of parenteral administration are generally advantageous. The instant invention can also be carried out by delivering the compound of formula I subcutaneously, intranasally, intrarectally, transdermally or intravaginally.

The compounds of formula I may also be administered by inhalation. By 'inhalation' is meant intranasal and oral inhalation administration. Appropriate dosage forms for such administration, such as an aerosol formulation or a metered dose inhaler, may be prepared by convention techniques.

The invention also relates to a pharmaceutical composition comprising a compound of formula I and a pharmaceutically acceptable carrier. The compounds of formula I may also be included in pharmaceutical compositions in combination with a second therapeutically active compound.

The pharmaceutical carrier employed may be, for example, either a solid, liquid or gas. Examples of solid carriers include lactose, terra alba, sucrose, talc, gelatin, agar, pectin, acacia, magnesium stearate, stearic acid and the like. Examples of liquid carriers are syrup, peanut oil, olive oil, water and the like. Examples of gaseous carriers include carbon dioxide and nitrogen.

Similarly, the carrier or diluent may include time delay material well known in the art, such as glyceryl monostearate or glyceryl distearate, alone or with a wax.

A wide variety of pharmaceutical dosage forms can be employed. If a solid dosage is used for oral administration, the preparation can be in the form of a tablet, hard gelatin capsule, troche or lozenge. The amount of solid carrier will vary widely, but generally will be from about 0.025 mg to about 1 g. When a liquid dosage form is desired for oral administration, the preparation is typically in the form of a syrup, emulsion, soft gelatin capsule, suspension or solution. When a parenteral dosage form is to be employed, the drug may be in solid or liquid form, and may be formulated for administration directly or may be suitable for reconstitution.

Topical dosage forms are also included. Examples of topical dosage forms are solids, liquids and semi-solids. Solids would include dusting powders, poultices and the like. Liquids include solutions, suspensions and emulsions. Semi-solids include creams, ointments, gels and the like.

The amount of a compound of formula I used topically will, of course, vary with the compound chosen, the nature and severity of the condition, and can be varied in accordance with the discretion of the physician. A representative, topical, dose of a compound of formula I is from as low as about 0.01 mg to as high as about 2.0 g, administered one to four, or, advantageously, one to two times daily.

The active ingredient may comprise, for topical administration, from about 0.001% to about 10% w/w.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container aseptically. Examples of bactericidal and fungicidal agents suitable for inclusion in the drops are phenyhnercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous liquid, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surfactant such as sorbitan esters or polyoxyethylene derivatives thereof. Suspending agents such as natural gums, cellulose derivatives or inorganic materials such as silicas, and other ingredients such as lanolin may also be included.

For inhaled formulations, the dosage amount per administration is generally lower than that for an oral formulation such as a tablet or capsule. For example, a daily dose of the active compound administered via an inhaled formulation may range from 0.010 mg to 10 mg, and particularly from 0.010 mg to 2.5 mg. Single or multiple inhaled doses may be used per day, but a single inhaled dose is preferred.

For administration by inhalation, the salts of Compounds of formula I of the present invention are conveniently delivered in the form of an aerosol suitable for pulmonary drug delivery. These aerosol dosage forms include but are not limited to nebulized solutions and suspensions, metered-dose inhalers or dry powder inhalers. For nebulization the active ingredient(s) are typically formulated in an aqueous vehicle and administered by jet or electronic devices capable of generating a fine aerosol cloud. Metered-dose inhalers (MDI) use propellants such as hydrofluorocarbons to solubilize or suspend the active ingredient in a pressurized container capable of generating the disperse aerosol. For dry powder inhalation, the salts of Compounds of formula I are used alone or with excipients in conjunction with a delivery device capable for delivery of the active substance to the lung.

In one embodiment the medicinal preparation is adapted for use with a pressurized metered dose inhaler which releases a metered dose of medicine upon each actuation. The formulation for pMDIs can be in the form of solutions or suspensions in halogenated hydrocarbon propellants. The type of propellant being used in pMDIs is being shifted to hydrofluoroalkanes (HFAs), also known as hydrofluorocarbons (HFCs) as the use of chlorofluorocarbons (known also as Freons or CFCs) is being phased out. In particular, 1,1,1,2-tetrafluoroethane (HFA 134a) and 1,1,1,2,3,3,3-heptafluoropropane (HFA 227) are used in several currently marketed pharmaceutical inhalation products. The composition may include other pharmaceutically acceptable excipients for inhalation use such as ethanol, oleic acid, polyvinylpyrrolidone and the like, Pressurized MDIs typically have two components. Firstly, there is a canister component in which the drug particles are stored under pressure in a suspension or solution form. Secondly, there is a receptacle component used to hold and actuate the canister. Typically, a canister will contain multiple doses of the formulation, although it is possible to have single dose canisters as well. The canister component typically includes a valve outlet from which the contents of the canister can be discharged. Aerosol medication is dispensed from the pMDI by applying a force on the canister component to push it into the receptacle component thereby opening the valve outlet and causing the medication particles to be conveyed from the valve outlet through the receptacle component and discharged from an outlet of the receptacle. Upon discharge from the canister, the medication particles are "atomized", forming an aerosol. It is intended that the patient coordinate the discharge of aerosolized medication with his or her inhalation, so that the medication particles are entrained in the patient's aspiratory flow and conveyed to the lungs. Typically, pMDIs use propellants to pressurize the contents of the canister and to propel the medication particles out of the outlet of the receptacle component. In pMDIs, the formulation is provided in a liquid or suspension form, and resides within the container along with the propellant. The propellant can take a variety of forms. For example, the propellant can comprise a compressed gas or liquefied gas.

In another embodiment the medicinal preparation is adapted for use with a dry powder inhaler. The inhalation composition suitable for use in DPIs typically comprises particles of the active ingredient and particles of a pharmaceutically acceptable carrier. The particle size of the active material may vary from about 0.1 μm to about 10 μm; however, for effective delivery to the distal lung, at least 95 percent of the active agents particles are 5 prri or smaller. Each of the active agent can be present in a concentration of 0.01-99%. Typically however, each of the active agents is present in a concentration of about 0.05 to 50%, more typically about 0.2-20% of the total weight of the composition.

As noted above, in addition to the active ingredients, the inhalable powder preferably includes pharmaceutically acceptable carrier, which may be composed of any pharmacologically inert material or combination of materials which is acceptable for inhalation. Advantageously, the carrier particles are composed of one or more crystalline sugars; the carrier particles may be composed of one or more sugar alcohols or polyols. Preferably, the carrier particles are particles of dextrose or lactose, especially lactose. In embodiments of the present invention which utilize conventional dry powder inhalers, such as the Rotohaler, Diskhaler, and Turbohaler, the particle size of the carrier particles may range from about 10 microns to about 1000 microns. In certain of these embodiments, the particle size of the carrier particles may range from about 20 microns to about 120 microns. In certain other embodiments, the size of at least 90% by weight of the carrier particles is less than 1000 microns and preferably lies between 60 microns and 1000 microns. The relatively large size of these carrier particles gives good flow and entrainment characteristics. Where present, the amount of carrier particles will generally be up to 95%, for example, up to 90%, advantageously up to 80% and preferably up to 50% by weight based on the total weight of the powder. The amount of any fine excipient material, if present, may be up to 50% and advantageously up to 30%, especially up to 20%, by weight, based on the total weight of the powder.

The present invention in one embodiment provides a composition for use in dry powder inhaler, which comprises montelukast acid and a Compound of Formula I, and lactose for inhalation as a carrier, wherein said composition is adapted for simultaneous, sequential or separate administration of the active agents. The weight ratio of lactose to montelukast acid is from about 1:1 to about 30:1, and to Compound X is from about 20:1 to about 30:1. In one instance the weight ratio of lactose to montelukast acid is about 2:1 to about 25:1, and to Compound of formula I is about 20:1 to about 25:1.

The present invention in one embodiment provides a composition for use in dry powder inhaler, which comprises montelukast acid and an inhaled corticosteroid, and lactose for inhalation as a carrier, wherein said composition is adapted for simultaneous, sequential or separate administration of the active agents. In such compositions the weight ratio of lactose to montelukast acid is generally from about 1:1 to about 30:1. In a composition where the inhaled corticosteroid is mometasone furoate, the weight ratio of lactose to mometasone furoate is from about 130:1 to about 4:1, and in one embodiment the ratio is from about 124:1 to about 60:1. In a composition where the inhaled corticosteroid is ciclesonide, the weight ratio of lactose to ciclesonide is about 350:1 to about 100:1.

The powder may also contain fine particles of an excipient material, which may for example be a material such as one of those mentioned above as being suitable for use as a carrier material, especially a crystalline sugar such as dextrose or lactose. The fine excipient material may be of the same or a different material from the carrier particles, where both are present. The particle size of the fine excipient material will generally not exceed 30 μm, and preferably does not exceed 20 μm. In some circumstances, for example, where any carrier particles and/or any fine excipient material present is of a material itself capable of inducing a sensation in the oropharyngeal region, the carrier particles and/or the fine excipient material can constitute the indicator material. For example, the carrier particles and/or any fine particle excipient may comprise mannitol.

The formulations described herein may also include one or more additives, in an amount from about 0.1% to about 10% by weight, and preferably from about 0.15% to 5%, most preferably from about 0.5% to about 2%. Additives may include, for example, magnesium stearate, leucine, lecithin, and sodium stearyl fumarate. When the additive is micronized leucine or lecithin, it is preferably provided in an amount from about 0.1% to about 10% by weight, preferably about 0.5% to about 5%, preferably about 2%, of micronized leucine. Preferably, at least 95% by weight of the micronized leucine has a particle diameter of less than 150 microns, preferably less than 100 microns, and most preferably less than 50 microns. Preferably, the mass median diameter of the micronized leucine is less than 10 microns.

If magnesium stearate or sodium stearyl fumarate is used as the additive, it is preferably provided in an amount from about 0.05% to about 5%, preferably from about 0.15% to about 2%, most preferably from about 0.25 to about 0.5%.

Where reference is made to particle size of particles of the powder, it is to be understood, unless indicated to the contrary, that the particle size is the volume weighted particle size. The particle size may be calculated by a laser diffraction method. Where the particle also includes an indicator material on the surface of the particle, advantageously the particle size of the coated particles is also within the preferred size ranges indicated for the uncoated particles.

The dry powder pharmaceutical compositions in accordance with this invention may be prepared using standard methods. The pharmaceutically active agents, carrier particles, and other excipients, if any, may be intimately mixed using any suitable blending apparatus, such as a tumbling mixer. The particular components of the formulation can be admixed in any order. Pre-mixing of particular components may be found to be advantageous in certain circumstances. The powder mixture is then used to fill capsules, blisters, reservoirs, or other storage devices for use in conjunction with dry powder inhalers.

In a dry powder inhaler, the dose to be administered is stored in the form of a non-pressurized dry powder and, on actuation of the inhaler; the particles of the powder are inhaled by the patient. DPIs can be unit-dose devices in which the powder is contained in individual capsules, multiple-unit dose in which multiple capsules or blisters are used, and reservoir devices in which the powder is metered at dosing time from a storage container. Dry powder inhalers can be "passive" devices in which the patient's breath is used to disperse the powder for delivery to the lungs, or "active" devices in which a mechanism other than breath actuation is used to disperse the powder. Examples of "passive" dry powder inhaler devices include the Spinhaler, Handihaler, Rotahaler, Diskhaler, Diskus, Turbuhaler, Clickhaler, etc.

Examples of active inhalers include Nektar Pulmonary Inhaler (Nektar Therapeutics), Veetura Limited's Aspirair™ device, Microdose DPI (MicroDose), and Oriel DPI (Oriel). It should be appreciated, however, that the compositions of the present invention can be administered with either passive or active inhaler devices.

Assays

Protein Expression and Purification.

Murine p38 containing the FLAG epitope tag was expressed in *Drosophila* S2 cells under transcriptional control of a copper-inducible metallothionein promoter. Expression of recombinant p38 was induced by treating transfected cells with 1 mM CuSO4 for 4 hours. To generate active recombinant murine p38, CuSO4-treated S2 cells were stimulated 10 minutes prior to harvest with 400 mM NaCl, 2 mM Na3VO4, and 100 □g/L okadaic acid. Cell pellets were washed with phosphate-buffered saline, 2 mM Na3VO4, and lysed in 20 mM Tris HCl, pH 7.5, 120 mM NaCl, 1% Triton X-100, 2 mM EDTA, 20 mM NaF, 4 mM Na3VO4, 2 mM Prefabloc SC (Boehringer Mannheim). Cell lysates were centrifuged for 10 min at 13,000×g, and activated, recombinant murine p38 was immunoaffinity purified from the lysate by column chromatography through anti-FLAG M2 resin (Kodak) that had been equilibrated with lysis buffer. After loading the extract the resin was washed with 10 column volumes of lysis buffer, 10 column volumes buffer A (10 mM Tris HCl, pH 7.5, 500 mM NaCl, 20% glycerol) and 10 column volumes of buffer B (10 mM Tris HCl pH 7.5, 150 mM NaCl, 20% glycerol). The fusion protein was eluted in buffer B containing 100 μg/mL FLAG peptide (Kodak).

The N-terminal 115 amino acids of ATF-2 was expressed in *E. coli* as a fusion protein with glutathione-S-transferase. The fusion protein was purified over glutathione agarose according to standard procedures (Pharmacia).

p38 Kinase Assay.

p38 kinase assays were performed in a reaction volume of 100 μL in a 96-well plate, at 30° for 45-1200 min under the following conditions: 25 mM Hepes, pH 7.4, 10 mMmgCl2, 20 mM β-glycerolphosphate, 2 mM DTT, 5 μM ATP, 10 μCi [γ-33P]-ATP and ~2 μM GST-ATF2. Serial dilutions of compounds were added to each reaction in 2 μL DMSO. 2 μL of DMSO was added to the last row of each reaction plate as the no inhibitor control for each inhibitor titration. The reaction was terminated with an equal volume of a stop solution containing 100 mM EDTA and 15 mM sodium pyrophosphate. PVDF filter plates (MAIPNOB50, Millipore) were pre-wet with methanol and washed with the stop solution. 50 υL aliquots from a single reaction were applied to the filter under vacuum, and the filter was washed twice with 75 mM phosphoric acid. The filter plates were counted in a scintillation counter (Top Count, Packard) and the percent inhibition at each compound concentration is determined.

Alternatively, p38 kinase assays were performed in a reaction volume of 70υL in a 384-well plate, at 30° for 45-1220 mM under the following conditions: 50 mM Hepes, pH 7.4, 10 mM MgCl2, 1 mg/ml FA Free BSA, 1 mM DTT, 10 μM ATP, 10 μM p38 peptide [Caliper Life Sciences FL-Peptide 8 (5-FAM-IPTSPITTTYFFEKKK-COOH)] and 5.7 nM p38-α (Millipore), or 14.3 nM unactivated MAPKAP kinase-2, 0.18 nM p38-α (Millipore) and 2 uM RSK peptide [Caliper Life Sciences FL-Peptide 11 (5-FAM-KKLNRTLSVA-COOH)]. Serial dilutions of compounds were added to each reaction in 700 nL DMSO. 700 nL of DMSO was added to the control wells of the reaction plate as the no inhibitor control for each inhibitor titration. The reaction was terminated by the addition of 15 μL of a 100 mM EDTA. Product formation was analyzed using the Caliper LabChip 3000. The Separation buffer contained 100 mM HEPES pH 7.5, 0.015% Brij-35, 2.5% Coating Reagent #3 (Caliper Life Sciences) and 10 mM EDTA. Calculation of the substrate product ratios are performed using the HTS Well Analyzer software provided by Caliper Life Sciences and the percent inhibition at each compound concentration is determined.

TNF-α Release Assay.

Blood was obtained from healthy volunteers by venipuncture using sodium heparin as an anti-coagulant. Peripheral blood mononuclear cells (PBMCs) were isolated using Lymphocyte Separation Medium (ICN) according to manufacturers specifications. Isolated PBMCs were washed 3 times with HBSS and diluted to a density of 2×106 cells/mL in RPMI + 5% autologous human serum. 50 μL of the serial dilutions of inhibitor were added to wells of a 96-well tissue culture plate followed by addition of 100 μL of PBMCs and then 50 μl of RPMI complete medium containing 400 ng/mL LPS. A control well of cells without compound but with LPS (maximal stimulation control) and one without compound and without LPS (background control) were included in each titration. The cells were incubated for 16 hours in a humidified incubator at 37° C., 5% $CO_2$. Supernatants were then harvested and TNF-α levels were quantified by immunoassay using commercial reagents (R&D, Inc).

The compounds of this invention, and in particular the Examples, demonstrated efficacy (IC50) in the above assays by results of less than 10 μM. Advantageous compounds had results less than 1 μM. Even more advantageous compounds had results less than 0.1 μM. Still more advantageous compounds had results in the assays of less than 0.01 μM. The follow are illustrative of the efficacy demonstrated by the specific Examples:

Structures of Compounds 1-46 and in vitro Activities of Compounds

| Example | Structure | $IC_{50}$ p38a*peptide [nM] | $IC_{50}$ hWB [nM] |
|---|---|---|---|
| 1 | 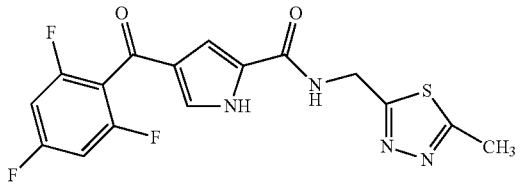 [SMILES: Cc1nnc(CNC(=O)c2cc(C(=O)c3c(F)cc(F)cc3F)c[nH]2)s1] | 167 | 467 |

-continued

| Example | Structure | IC$_{50}$ p38a*peptide [nM] | IC$_{50}$ hWB [nM] |
|---|---|---|---|
| 2 | 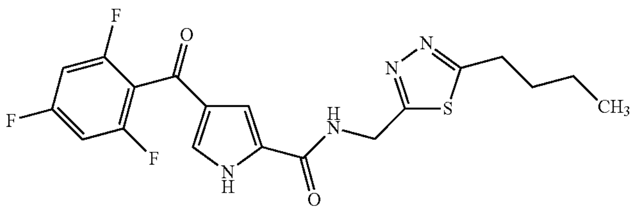 [SMILES: CCCCc1nnc(CNC(=O)c2cc(C(=O)c3c(F)cc(F)cc3F)c[nH]2)s1] | 441 | 4220 |
| 3 | 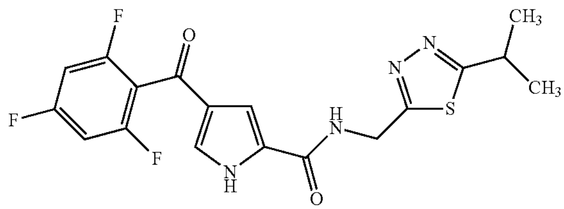 [SMILES: CC(C)c1nnc(CNC(=O)c2cc(C(=O)c3c(F)cc(F)cc3F)c[nH]2)s1] | 479 | |
| 4 | 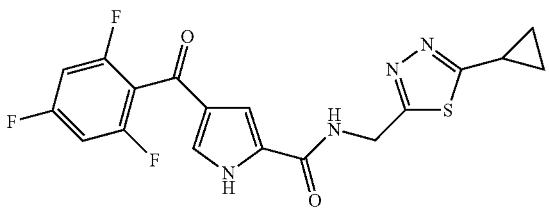 [SMILES: O=C(NCc1nnc(C2CC2)s1)c1cc(C(=O)c2c(F)cc(F)cc2F)c[nH]1] | 73 | 330 |
| 5 | 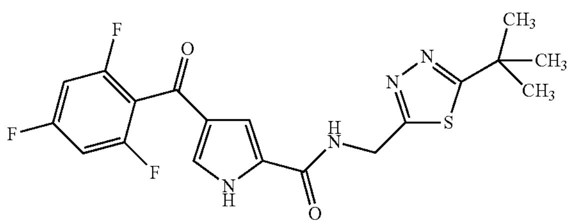 [SMILES: CC(C)(C)c1nnc(CNC(=O)c2cc(C(=O)c3c(F)cc(F)cc3F)c[nH]2)s1] | 608 | |
| 6 | 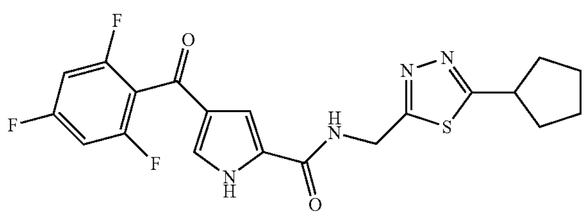 [SMILES: O=C(NCc1nnc(C2CCCC2)s1)c1cc(C(=O)c2c(F)cc(F)cc2F)c[nH]1] | 1510 | 2870 |
| 7 | 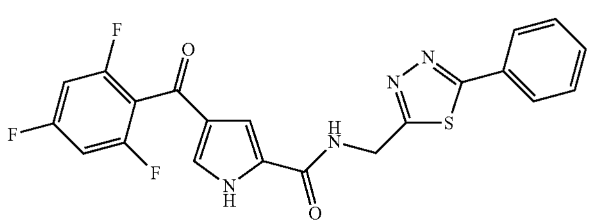 [SMILES: O=C(NCc1nnc(-c2ccccc2)s1)c1cc(C(=O)c2c(F)cc(F)cc2F)c[nH]1] | 42 | 4350 |
| 8 | 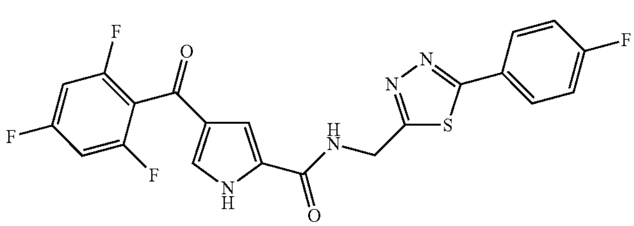 [SMILES: O=C(NCc1nnc(-c2ccc(F)cc2)s1)c1cc(C(=O)c2c(F)cc(F)cc2F)c[nH]1] | 50 | 1000 |

-continued

| Example | Structure | IC$_{50}$ p38a*peptide [nM] | IC$_{50}$ hWB [nM] |
| --- | --- | --- | --- |
| 9 | 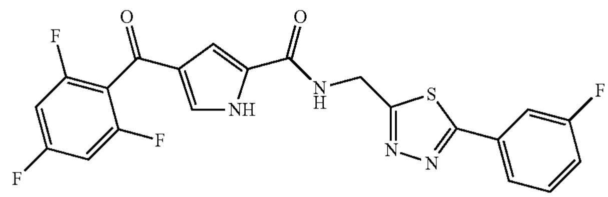 [SMILES: O=C(NCc1nnc(-c2cccc(F)c2)s1)c1cc(C(=O)c2c(F)cc(F)cc2F)c[nH]1] | 462 | 3490 |
| 10 | 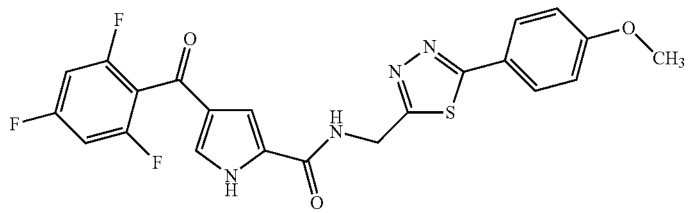 [SMILES: COc1ccc(-c2nnc(CNC(=O)c3cc(C(=O)c4c(F)cc(F)cc4F)c[nH]3)s2)cc1] | 31 | |
| 11 | 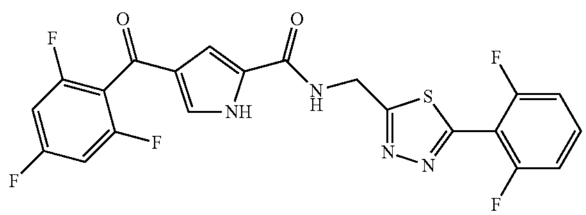 [SMILES: O=C(NCc1nnc(-c2c(F)cccc2F)s1)c1cc(C(=O)c2c(F)cc(F)cc2F)c[nH]1] | 276 | 2850 |
| 12 | 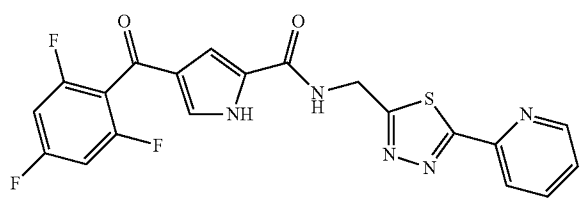 [SMILES: O=C(NCc1nnc(-c2ccccn2)s1)c1cc(C(=O)c2c(F)cc(F)cc2F)c[nH]1] | 66 | 570 |
| 13 | 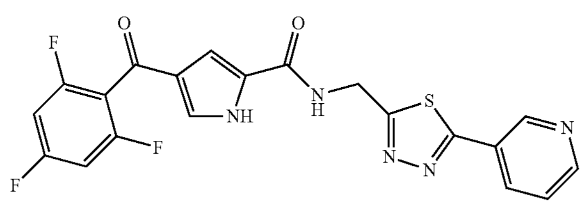 [SMILES: O=C(NCc1nnc(-c2cccnc2)s1)c1cc(C(=O)c2c(F)cc(F)cc2F)c[nH]1] | 40 | 747 |
| 14 | 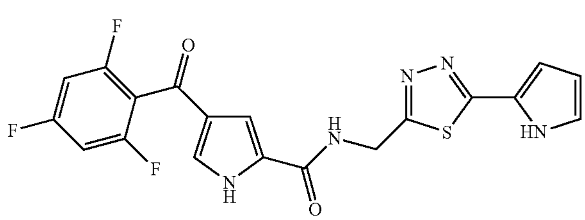 [SMILES: O=C(NCc1nnc(-c2ccc[nH]2)s1)c1cc(C(=O)c2c(F)cc(F)cc2F)c[nH]1] | 121 | 1270 |
| 15 | 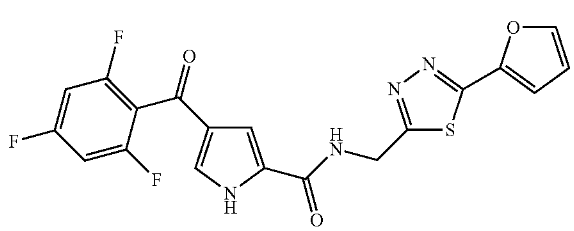 [SMILES: O=C(NCc1nnc(-c2ccco2)s1)c1cc(C(=O)c2c(F)cc(F)cc2F)c[nH]1] | 98 | 614 |

-continued
| Example | Structure | IC$_{50}$ p38a*peptide [nM] | IC$_{50}$ hWB [nM] |
|---|---|---|---|
| 16 | 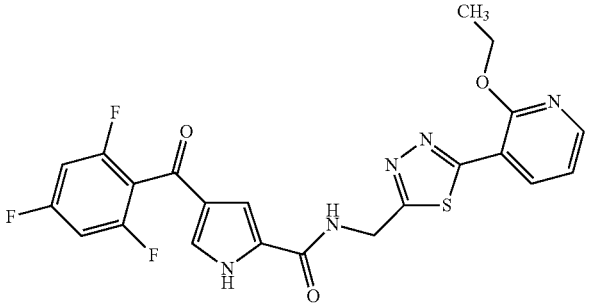 [SMILES: CCOc1ncccc1-c1nnc(CNC(=O)c2cc(C(=O)c3c(F)cc(F)cc3F)c[nH]2)s1] | 135 | |
| 17 | 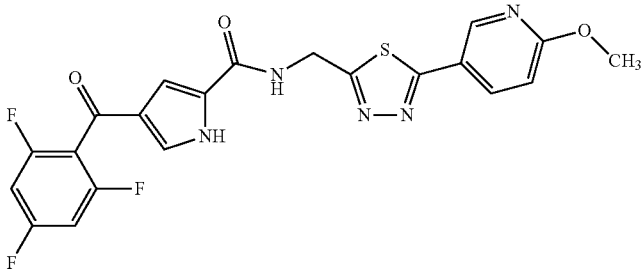 [SMILES: COc1ccc(-c2nnc(CNC(=O)c3cc(C(=O)c4c(F)cc(F)cc4F)c[nH]3)s2)cn1] | 78 | 2820 |
| 18 | 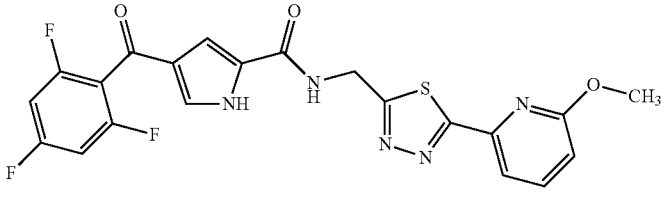 [SMILES: COc1cccc(-c2nnc(CNC(=O)c3cc(C(=O)c4c(F)cc(F)cc4F)c[nH]3)s2)n1] | 94 | |
| 19 | 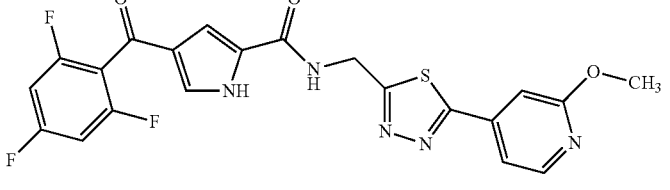 | 85 | |
| 20 | 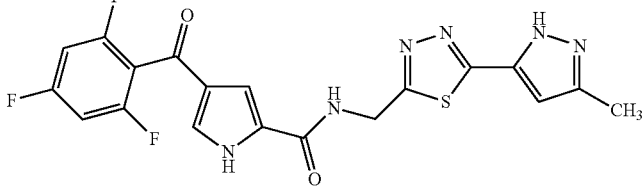 | 22 | 262 |
| 21 | 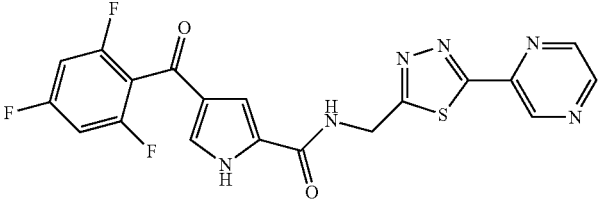 [SMILES: O=C(NCc1nnc(-c2cnccn2)s1)c1cc(C(=O)c2c(F)cc(F)cc2F)c[nH]1] | 78 | 815 |

-continued

| Example | Structure | IC$_{50}$ p38a*peptide [nM] | IC$_{50}$ hWB [nM] |
|---|---|---|---|
| 22 | 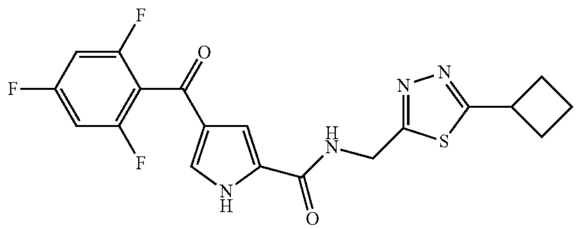 [SMILES: O=C(NCc1nnc(C2CCC2)s1)c1cc(C(=O)c2c(F)cc(F)cc2F)c[nH]1] | 489 | |
| 23 | 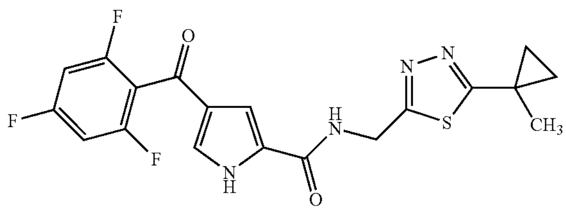 [SMILES: CC1(c2nnc(CNC(=O)c3cc(C(=O)c4c(F)cc(F)cc4F)c[nH]3)s2)CC1] | 826 | |
| 24 | 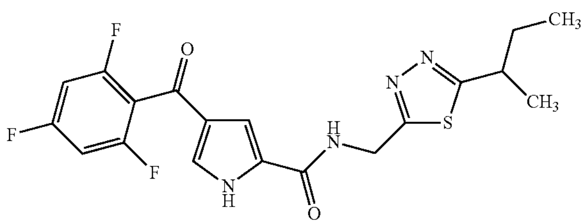 [SMILES: CCC(C)c1nnc(CNC(=O)c2cc(C(=O)c3c(F)cc(F)cc3F)c[nH]2)s1] | 1018 | |
| 25 | 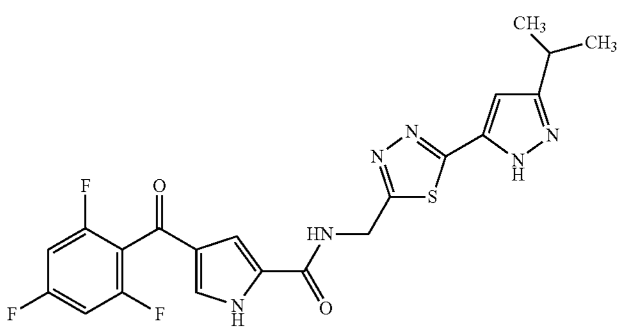 [SMILES: CC(C)c1cc(-c2nnc(CNC(=O)c3cc(C(=O)c4c(F)cc(F)cc4F)c[nH]3)s2)[nH]n1] | 10 | 90 |
| 26 | 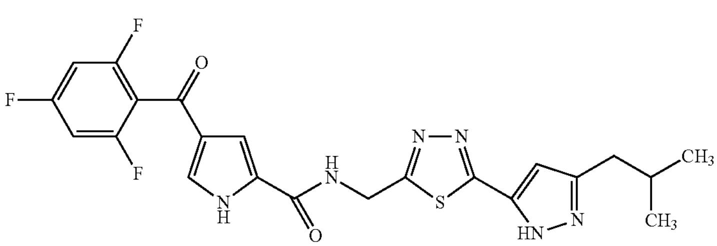 [SMILES: CC(C)Cc1cc(-c2nnc(CNC(=O)c3cc(C(=O)c4c(F)cc(F)cc4F)c[nH]3)s2)[nH]n1] | 24 | 163 |
| 27 | 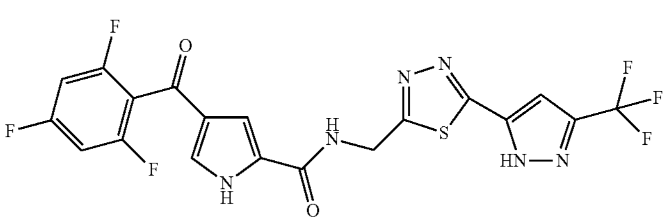 [SMILES: O=C(NCc1nnc(-c2cc(C(F)(F)F)n[nH]2)s1)c1cc(C(=O)c2c(F)cc(F)cc2F)c[nH]1] | 1400 | |

-continued

| Example | Structure | IC$_{50}$ p38a*peptide [nM] | IC$_{50}$ hWB [nM] |
|---|---|---|---|
| 28 | 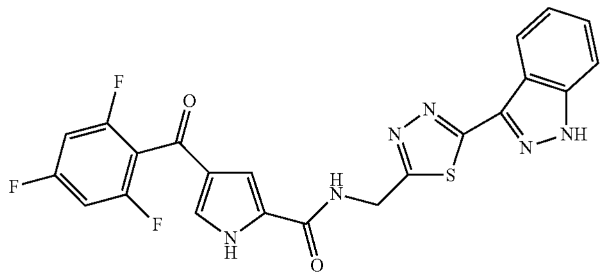 [SMILES: O=C(NCc1nnc(-c2n[nH]c3ccccc23)s1)c1cc(C(=O)c2c(F)cc(F)cc2F)c[nH]1] | 69 | 360 |
| 29 | 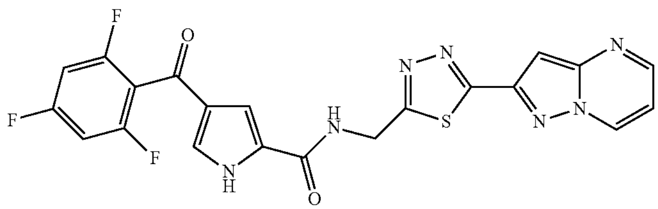 [SMILES: O=C(NCc1nnc(-c2cc3ncccn3n2)s1)c1cc(C(=O)c2c(F)cc(F)cc2F)c[nH]1] | 17 | 885 |
| 30 | 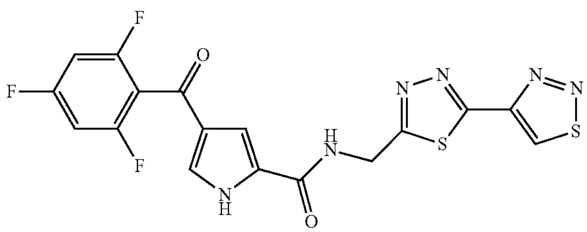 [SMILES: O=C(NCc1nnc(-c2csnn2)s1)c1cc(C(=O)c2c(F)cc(F)cc2F)c[nH]1] | 634 | |
| 31 | 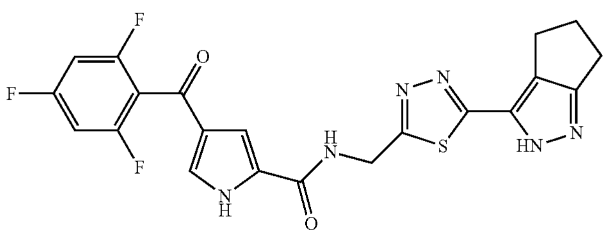 [SMILES: O=C(NCc1nnc(-c2[nH]nc3c2CCC3)s1)c1cc(C(=O)c2c(F)cc(F)cc2F)c[nH]1] | 36 | |
| 32 | 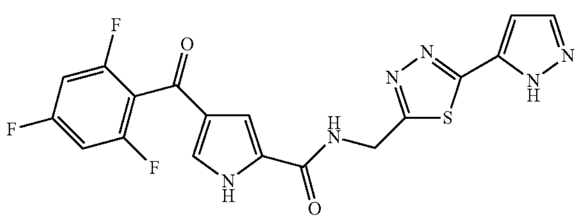 [SMILES: O=C(NCc1nnc(-c2ccn[nH]2)s1)c1cc(C(=O)c2c(F)cc(F)cc2F)c[nH]1] | 43 | 84 |
| 33 | 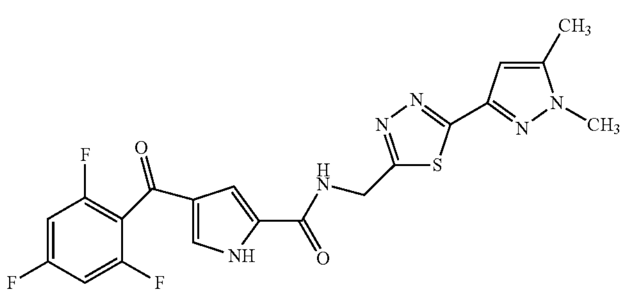 [SMILES: Cc1cc(-c2nnc(CNC(=O)c3cc(C(=O)c4c(F)cc(F)cc4F)c[nH]3)s2)nn1C] | 35.11 | |

-continued

| Example | Structure | IC₅₀ p38a*peptide [nM] | IC₅₀ hWB [nM] |
|---|---|---|---|
| 34 | 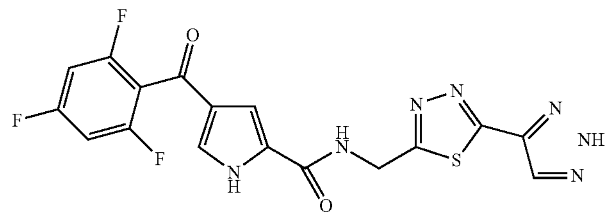 | 179.9 | |
| 35 | 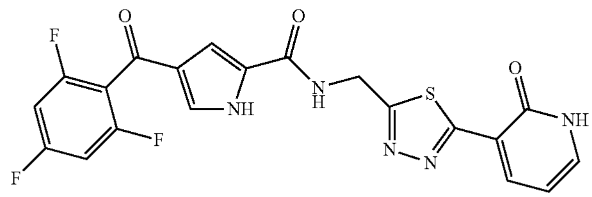 [SMILES: O=C(NCc1nnc(-c2ccc[nH]c2=O)s1)c1cc(C(=O)c2c(F)cc(F)cc2F)c[nH]1] | 37.45 | 167.5 |
| 36 | 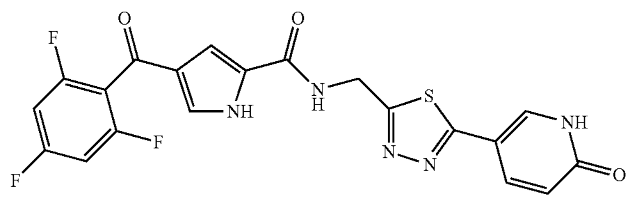 [SMILES: O=C(NCc1nnc(-c2ccc(=O)[nH]c2)s1)c1cc(C(=O)c2c(F)cc(F)cc2F)c[nH]1] | 70.36 | |
| 37 | 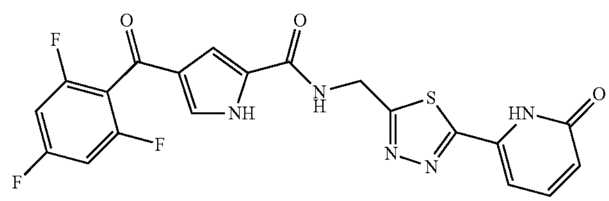 [SMILES: O=C(NCc1nnc(-c2cccc(=O)[nH]2)s1)c1cc(C(=O)c2c(F)cc(F)cc2F)c[nH]1] | 172.9 | |
| 38 | 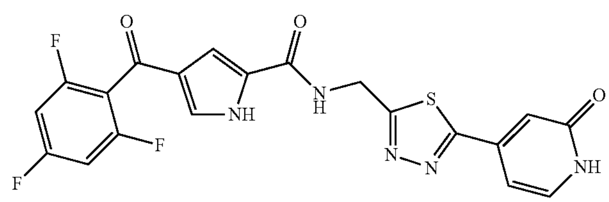 [SMILES: O=C(NCc1nnc(-c2cc[nH]c(=O)c2)s1)c1cc(C(=O)c2c(F)cc(F)cc2F)c[nH]1] | 26.89 | |
| 39 | 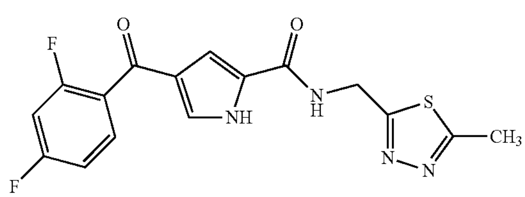 [SMILES: Cc1nnc(CNC(=O)c2cc(C(=O)c3ccc(F)cc3F)c[nH]2)s1] | 222.4 | |
| 40 | 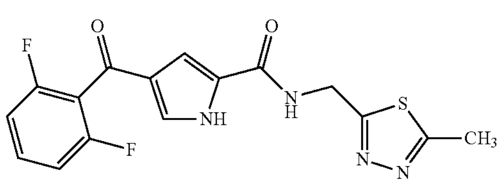 [SMILES: Cc1nnc(CNC(=O)c2cc(C(=O)c3c(F)cccc3F)c[nH]2)s1] | 149.6 | |

-continued

| Example | Structure | IC₅₀ p38a*peptide [nM] | IC₅₀ hWB [nM] |
|---|---|---|---|
| 41 | 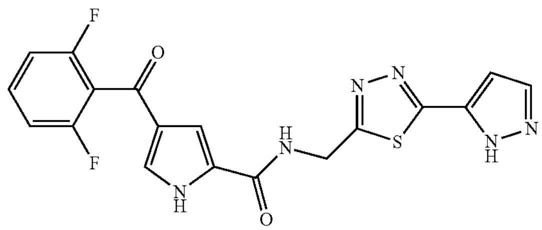 [SMILES: O=C(NCc1nnc(-c2ccn[nH]2)s1)c1cc(C(=O)c2c(F)cccc2F)c[nH]1] | | |
| 42 | 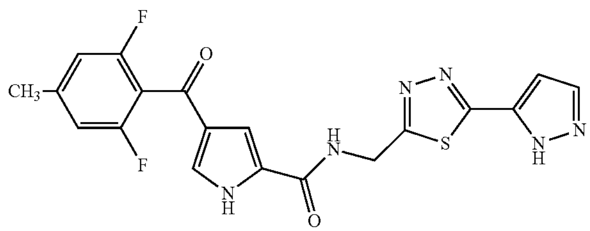 [SMILES: Cc1cc(F)c(C(=O)c2c[nH]c(C(=O)NCc3nnc(-c4ccn[nH]4)s3)c2)c(F)c1] | | |
| 43 | 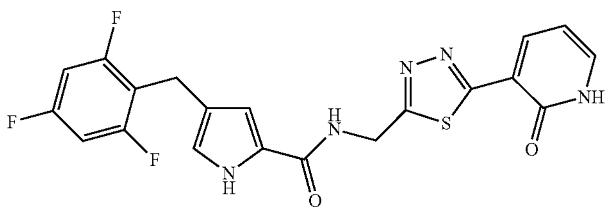 [SMILES: O=C(NCc1nnc(-c2ccc[nH]c2=O)s1)c1cc(Cc2c(F)cc(F)cc2F)c[nH]1] | 259.1 | 1877 |
| 44 | 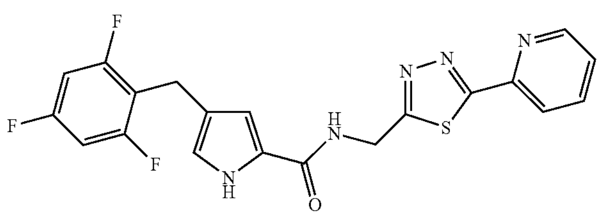 [SMILES: O=C(NCc1nnc(-c2ccccn2)s1)c1cc(Cc2c(F)cc(F)cc2F)c[nH]1] | 554.5 | |
| 45 | 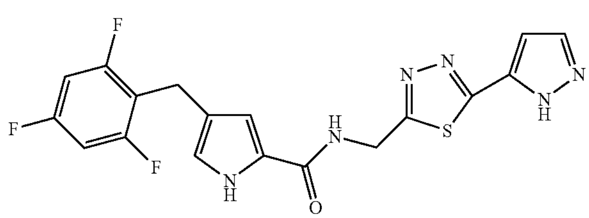 [SMILES: O=C(NCc1nnc(-c2ccn[nH]2)s1)c1cc(Cc2c(F)cc(F)cc2F)c[nH]1] | 353.6 | 1363 |
| 46 | 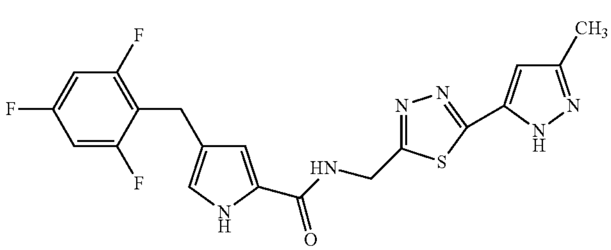 [SMILES: Cc1cc(-c2nnc(CNC(=O)c3cc(Cc4c(F)cc(F)cc4F)c[nH]3)s2)[nH]n1] | 242.9 | 3268 |

The abbreviations used herein are as follows unless specified otherwise:
Bu butyl
Bn benzyl
BOC t-butyloxycarbonyl
BOP benzotriazol-1-yloxy tris/dimethylamino-phosphonium hexafluorophosphate
DCC dicyclohexylcarbodiimide
DME 1,2-dimethoxyethane
DMF N,N-dimethylfoithamide
DMAP 4-dimethylaminopyridine
EDC 1-(3-dimethylaminopropyl_3-ethylcarbodi-imide hydrochloride
EtOAc ethyl acetate
Eq. equivalent(s)
HOBt, HOBT hydroxybenztriazole
HPLC high pressure liquid chromatography
LAH lithium aluminum hydride
LCMS liquid chromatography-mass spectrophotometer
LHMDS lithium bis(trimethylsilyl)amide
MeOH methanol
MHz megahertz
MS(ES) mass spectrophotometer-electon spray
NMP N-methylpyrrolidinone
Ph phenyl
Pr propyl
TBAF tetrabutylammonium fluoride
TEA triethylamine
THF tetrahydrofuran
TMEDA N,N,N',N'-tetramethylethylenediamine
TLC thin layer chromatography
Tetrakis tetrakis(triphenylphosphine)palladium The present compounds can be prepared according to the general Schemes provided below as well as the procedures provided in the Intermediates and Examples. The following Schemes, Examples and Intermediates further describe, but do not limit, the scope of the invention. The substituents are the same as in the above Formulas except where defined otherwise or otherwise apparent to the ordinary skilled artisan.

The procedures described herein for synthesizing the compounds may include one or more steps of protecting group manipulations and of purification, such as, recrystallization, distillation, column chromatography, flash chromatography, thin-layer chromatography (TLC), radial chromatography and high-pressure chromatography (HPLC). The products can be characterized using various techniques well known in the chemical arts, including proton and carbon-13 nuclear magnetic resonance ($^1$H and $^{13}$C NMR), infrared and ultraviolet spectroscopy (IR and UV), X-ray crystallography, elemental analysis and HPLC and mass spectrometry (LC-MS). Methods of protecting group manipulation, purification, structure identification and quantification are well known to one skilled in the art of chemical synthesis.

It is understood that the functional groups present in the compounds described in the Schemes below can be further manipulated, when appropriate, using the standard functional group transformation techniques available to those skilled in the art, to provide desired compounds described in this invention.

Other variations or modifications, which will be obvious to those skilled in the art, are within the scope and teachings of this invention. This invention is not to be limited except as set forth in the following claims.

The present compounds can be prepared according to the general Schemes provided below as well as the procedures provided in the Intermediates and Examples. The following Schemes, Examples and Intermediates further describe, but do not limit, the scope of the invention. The substituents are the same as in the above Formulas except where defined otherwise or otherwise apparent to the ordinary skilled artisan.

The procedures described herein for synthesizing the compounds may include one or more steps of protecting group manipulations and of purification, such as, recrystallization, distillation, column chromatography, flash chromatography, thin-layer chromatography (TLC), radial chromatography and high-pressure chromatography (HPLC). The products can be characterized using various techniques well known in the chemical arts, including proton and carbon-13 nuclear magnetic resonance ($^1$H and $^{13}$C NMR), infrared and ultraviolet spectroscopy (IR and UV), X-ray crystallography, elemental analysis and HPLC and mass spectrometry (LC-MS). Methods of protecting group manipulation, purification, structure identification and quantification are well known to one skilled in the art of chemical synthesis.

It is understood that the functional groups present in compounds described in the Schemes below can be further manipulated, when appropriate, using the standard functional group transformation techniques available to those skilled in the art, to provide desired compounds described in this invention.

Other variations or modifications, which will be obvious to those skilled in the art, are within the scope and teachings of this invention. This invention is not to be limited except as set forth in the following claims.

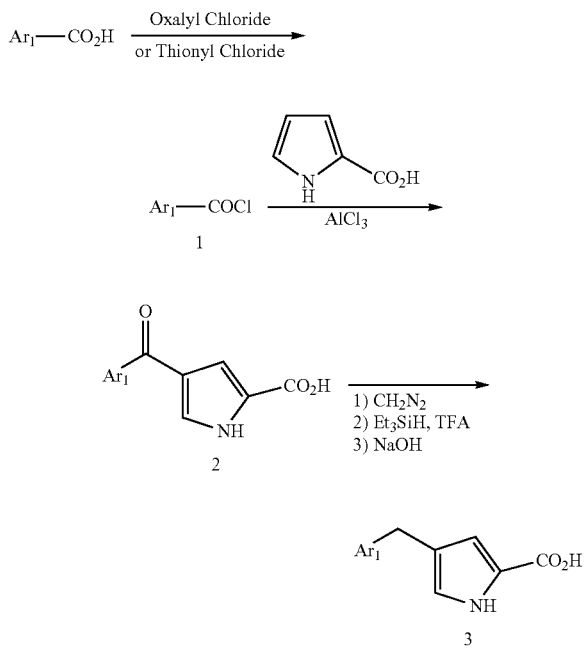

Scheme 1

Compounds of Formula I can be synthesized as described in Scheme 1, 2 and 3. The appropriate acid chloride 1 can be prepared by the method known to those skilled in the art from the corresponding acid or commercially available material. Compound 2 can be readily synthesized from the compound 1 by any of several known procedures such as Friedel-Crafts acylation with pyrrole-2-carboxylic acid of its ester derivatives. Compound 3 can be synthesized by reduction of the ketone with triethylsilane in TFA.

Scheme 2

Method A

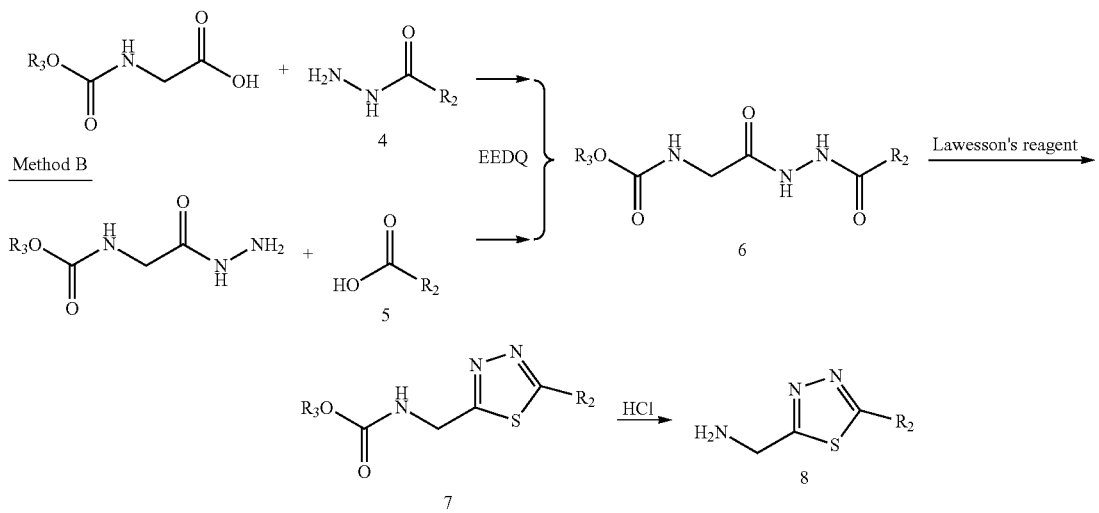

Method B

Method C

Compound 6 can be prepared from N-carbamoyl glycine and the appropriate carbohydrazide 4 (Method A), or N-carbamoyl glycine hydrazide and carboxylic acid 5 (Method B), using an amide bond formation reagent such as EEDQ. Treatment of compound 6 with Lawesson's reagent gives the thiadiazole compound 7. Deprotection of the carbamoyl group of compound 7 gives compound 8. Alternatively, compound 8 can be synthesized as described in Method C. Thus, an appropriately substituted carbohydrazide 4 was acylated by chloroacetyl chloride using base such as sodium bicarbonate to give compound 9. Treatment of compound 9 with Lawesson's reagent gives compound 10. The chlorine atom of compound 10 was displaced with an azide group and subsequent reduction of the azide group gives compound 8.

Scheme 3

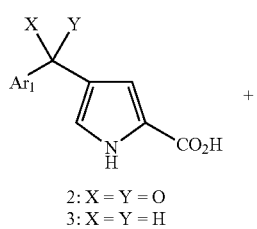

2: X = Y = O
3: X = Y = H

-continued

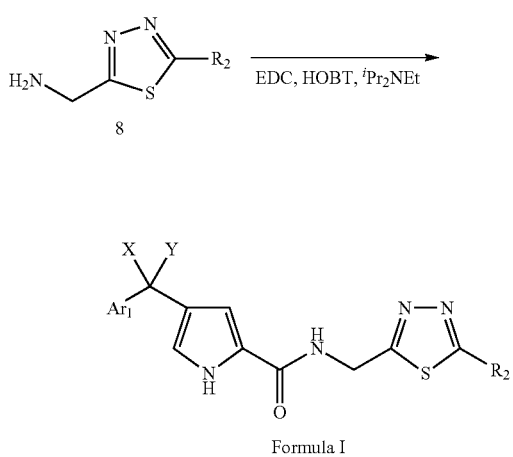

Under standard peptide coupling reaction conditions, the acid 2 or 3 and the amine 8 can be converted to the compound of Formula I. Standard peptide coupling reaction conditions mean coupling a carboxylic acid with an amine using an acid activating agent such as EDC, DCC or BOP in a suitable solvent such as methylene chloride or DMF in the present of HOBt.

Intermediate 1

4-(2,4,6-trifluorobenzoyl)-1H-pyrrole-2-carboxylic acid

Step A: 2,4,6-trifluorobenzoyl chloride

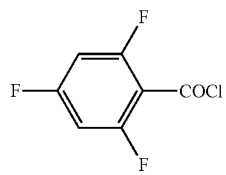 [SMILES: O=C(Cl)c1c(F)cc(F)cc1F]

To a DCM 200 mL solution of 2,4,6-trifluorobenzoic acid (20 g, 0.11 mol) and DMF (0.5 mL, 6.46 mmol) was added oxalyl chloride (21.6 g, 0.17 mol) dropwise. The reaction mixture was stirred at room temperature for 1 hr and the solvent was removed under reduced pressure to give the title compound as crude product (22 g).

Step B: 4-(2,4,6-trifluorobenzoyl)-1H-pyrrole-2-carboxylic acid

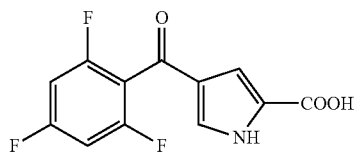 [SMILES: O=C(O)c1cc(C(=O)c2c(F)cc(F)cc2F)c[nH]1]

To a 120 mL dichloromethane solution of 2,4,6-trifluorobenzoyl chloride (4.3 g, 0.022 mol) was added $AlCl_3$ (8.8 g, 0.066 mol) under $N_2$ at room temperature. After stirring for 15 min, 1H-pyrrole-2-carboxylic acid (2.4 g, 0.022 mol) was added in small portions over a 10 min period. Stirring continued at room temperature for 1 hr, then the reaction mixture was treated with dropwise addition of ice-water (20 mL) and 1N HCl to adjust pH to 1. After stirring for another 30 min, the reaction mixture was extracted with AcOEt (3×30 mL). The combined organic layers were washed with brine, dried over anhydrous $Na_2SO_4$, filtered and concentrated to give the title compound (5.8 g, 97% yield). $^1$H-NMR (500 MHz, $CDCl_3$): δ 12.48 (br.s, 1H), 7.48 (s, 1H), 7.28-7.38 (m, 2H), 6.83 (s, 1H).

The following intermediates were prepared following the procedure for Intermediate 1, Steps A & B employing appropriately substituted carboxylic acids instead of 2,4,6-trifluorobenzoic acid.

Intermediate 2:
4-(2,6-difluorobenzoyl)-1H-pyrrole-2-carboxylic acid

Intermediate 3:
4-(2,4-difluorobenzoyl)-1H-pyrrole-2-carboxylic acid

Intermediate 4

4-(2,6-difluoro-4-methylbenzoyl)-1,1-pyrrole-2-carboxylic acid

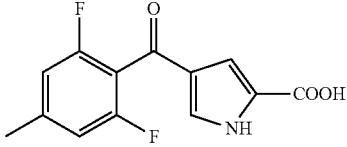 [SMILES: Cc1cc(F)c(C(=O)c2c[nH]c(C(=O)O)c2)c(F)c1]

Step A: 1,3-difluoro-5-methylbenzene

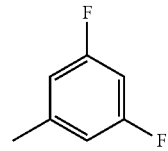

A mixture of 1-(bromomethyl)-3,5-difluorobenzene (50 g, 0.24 mol), 10% Pd/C (3 g) and sodium acetate (140 g, 1.7 mol) in anhydrous ether (250 mL) was stirred under hydrogen at atmospheric pressure for 24 hr. The mixture was filtered and the filtrate was dried over anhydrous $Na_2SO_4$, filtered, and then used directly in the next step. $^1$H NMR (500 MHz, $CDCl_3$): δ 6.56 (d, 2H, J=6.0 Hz), 6.47 (t, 1H, J=9.0 Hz), 2.22 (s, 3H).

Step B: 2,6-difluoro-4-methylbenzaldehyde

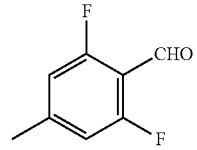

To a solution of 1,3-difluoro-5-methylbenzene (10.2 g, 80 mmol) in anhydrous ether (80 mL) was added n-BuLi (2.5 M solution in hexane, 48 ml, 120 mmol) over a 20 min period while the internal temperature was maintained at around −50° C. After stirring at that temperature for 1.5 hr, DMF (14.6 g, 200 mmol) was added over a 20 min period. After stirring at the same temperature for an additional 1.5 h, the reaction mixture was slowly poured into 1N aqueous sulfuric acid (300 mL) and extracted with ether three times. The combined organic layers were washed with brine, dried over anhydrous $MgSO_4$, filtered and concentrated to give the title compound (11.2 g, 90%). $^1$H-NMR (500 MHz, $CDCl_3$): δ 10.25 (s, 1H), 6.75 (d, 2H, J=9.9 Hz), 2.39 (s, 3H).

Step C: 2,6-difluoro-4-methylbenzoic acid

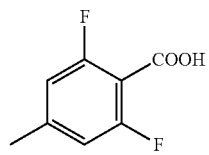

Silver oxide (43.8 g, 0.189 mol) was placed in a flask along with water (200 mL) and sodium hydroxide (33.7 g, 0.842 mol). To it was added 2,6-difluoro-4-methylbenzaldehyde (29.23 g, 0.187 mol) in small portions over a 30 min period. After a vigorous exothermic reaction, the color of the reaction mixture changed from black to gray. The resulting thick suspension was stirred for 1 hr and then filtered through a Buchner funnel. The filtrate was acidified to pH 2 with concentrated HCl to give a suspension. The precipitate was collected by suction filtration, dissolved in ether, dried over anhydrous $Na_2SO_4$, filtered and concentrated to give white solid (17.0 g, 53%). $^1$H-NMR (500 MHz, $d^6$-DMSO): δ13.7 (br.s, 1H), 7.02 (d, 2H, J=9.3 Hz), 2.32 (s, 3H).

Step D: 4-(2,6-difluoro-4-methylbenzoyl)-1H-pyrrole-2-carboxylic acid

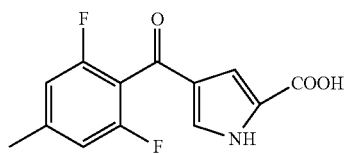 [SMILES: Cc1cc(F)c(C(=O)c2c[nH]c(C(=O)O)c2)c(F)c1]

Title compound was synthesized following the procedure for Intermediate 1, Step A & B, employing 2,6-difluoro-4-methylbenzoic acid instead of 2,4,6-trifluorobenzoic acid.
$^1$H-NMR (500 MHz, $d^6$-DMSO): δ 12.9 (br. s, 1H), 12.6 (s, 1H), 7.46 (s, 1H), 7.05 (d, 2H, J=8.8 Hz), 6.95 (s, 1H), 2.35 (s, 3H).

Intermediate 5

4-(2,4,6-trifluorobenzyl)-1H-pyrrole-2-carboxylic acid

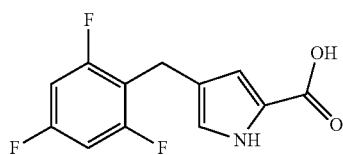 [SMILES: O=C(O)c1cc(Cc2c(F)cc(F)cc2F)c[nH]1]

Step A: methyl 4-(2,4,6-trifluorobenzoyl)-1H-pyrrole-2-carboxylate

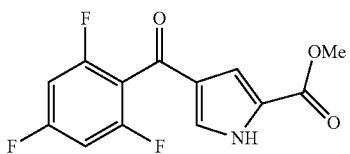 [SMILES: COC(=O)c1cc(C(=O)c2c(F)cc(F)cc2F)c[nH]1]

To a dichloromethane 70 mL suspension of 4-(2,4,6-trifluorobenzoyl)-1H-pyrrole-2-carboxylic acid (Intermediate 1) (3 g, 11.2 mmol) was added diazomethane solution in diethyl ether upon cooling in an ice-water bath. After stirring for 3 hr, the reaction mixture was concentrated and chromatographed on silica gel eluting with a gradient solvent mixture of AcOEt and hexanes to give the title compound (2.74 g).
$^1$H-NMR (500 MHz, $d^6$-DMSO): δ 12.9 (s, 1H), 7.65 (s, 1H), 7.34 (t, 2H, J=9 Hz), 7.08 (s, 1H), 3.79 (s, 3H).

Step B: methyl 4-(2,4,6-trifluorobenzyl)-1H-pyrrole-2-carboxylate

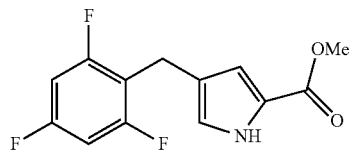 [SMILES: COC(=O)c1cc(Cc2c(F)cc(F)cc2F)c[nH]1]

To a TFA 30 mL solution of methyl 4-(2,4,6-trifluorobenzoyl)-1H-pyrrole-2-carboxylate in a sealed tube was added triethylsilane (2.55 g, 22 mmol). The resulting reaction mixture was heated in an oil bath at 70° C. overnight. The reaction was concentrated and diluted with isopropylacetate and saturated sodium bicarbonate aqueous solution. The organic layer was separated. The aqueous layer was extracted with isopropylacetate twice. The combined organic layers were dried over anhydrous sodium sulfate, filtered, concentrated and chromatographed on silica gel eluting with a gradient solvent mixture of AcOEt and hexanes to give the title compound (840 mg).
$^1$H-NMR (500 MHz, $d^6$-DMSO): δ 11.7 (s, 1H), 7.16 (t, 2H, J=9 Hz), 6.79 (s, 1H), 6.52 (s, 1H), 3.72 (s, 3.70 (s, 3H).

Step C: 4-(2,4,6-trifluorobenzyl)-1H-pyrrole-2-carboxylic acid

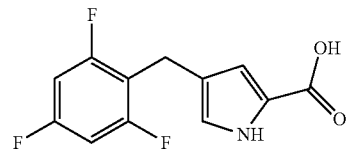 [SMILES: O=C(O)c1cc(Cc2c(F)cc(F)cc2F)c[nH]1]

To a methanol 30 mL solution of methyl 4-(2,4,6-trifluorobenzyl)-1H-pyrrole-2-carboxylate (840 mg, 3.1 mmol) was added 5N sodium hydroxide solution (3.1 mL, 16 mmol) and the reaction was stirred in an oil bath at 70° C. overnight. After cooling to rt, pH of the reaction mixture was adjusted to 1.5 to give a gray suspension. The precipitate was collected by suction filtration and dried under vacuum to give the title compound (796 mg).
$^1$H-NMR (500 MHz, $d^6$-DMSO): δ 12.2 (s, 1H), 11.5 (s, 1H), 7.15 (t, 2H, J=8 Hz), 6.73 (s, 1H), 6.47 (s, 1H), 3.73 (s, 2H).

EXAMPLE 1

N-[(5-methyl-1,3,4-thiadiazol-2-yl)methyl]-4-(2,4,6-trifluorobenzoyl)-1-H-pyrrole-2-carboxamide

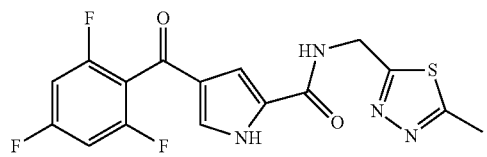 [SMILES: Cc1nnc(CNC(=O)c2cc(C(=O)c3c(F)cc(F)cc3F)c[nH]2)s1]

Step A: tert-butyl[2-(2-acetylhydrazino)-2-oxoethyl]carbamate

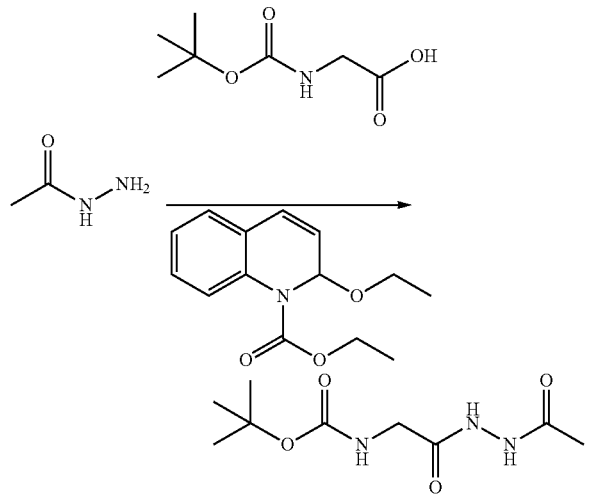

Under $N_2$ atmosphere, to a dichloromethane 10 mL solution of N-tert-butyloxycarbonyl-glycine (500 mg, 2.85 mmol) was added EEDQ (706 mg, 2.85 mmol). After stirring for 15 min, to it was added acethydrazide (260 mg, 3.51 mmol) and stirring continued at rt overnight. The precipitate was collected by suction filtration to give the title compound as white fluffy solid (496 mg).

$^1$H-NMR (CDCl$_3$, 400 MHz): δ 8.84 (brs, 1H), 8.27 (brs, 1H), 5.22 (brs, 1H), 3.87 (d, 2H), 2.02 (s, 3H), 1.41 (s, 9H).

Step B: tert-butyl[(5-methyl-1,3,4-thiadiazol-2-yl)methyl]carbamate

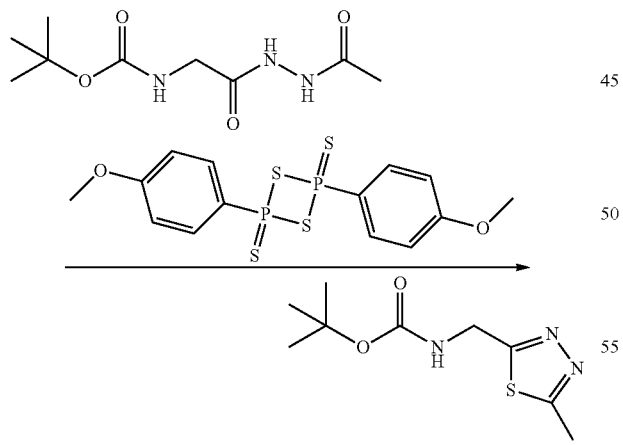

To a 37.5 mL THF solution of tert-butyl[2-(2-acetylhydrazino)-2-oxoethyl]carbamate (496 mg, 2.15 mmol) was added Lawesson's reagent (900 mg, 2.23 mmol). The resulting reaction mixture was heated to reflux for 3 hr. The reaction was concentrated and chromatographed on silica gel eluting with a gradient solvent mixture of AcOEt & dichloromethane to give the title compound as white crystalline solid (391 mg).

$^1$H-NMR (CDCl$_3$, 500 MHz): δ 5.31 (brs, 1H), 4.69 (d, 2H, J=6 Hz), 2.78 (s, 3H), 1.49 (s, 9H). LC/MS: m/z=230 (M+H), 252 (M+Na).

Step C: 1-(5-methyl-1,3,4-thiadiazol-2-yl)methanamine hydrochloride

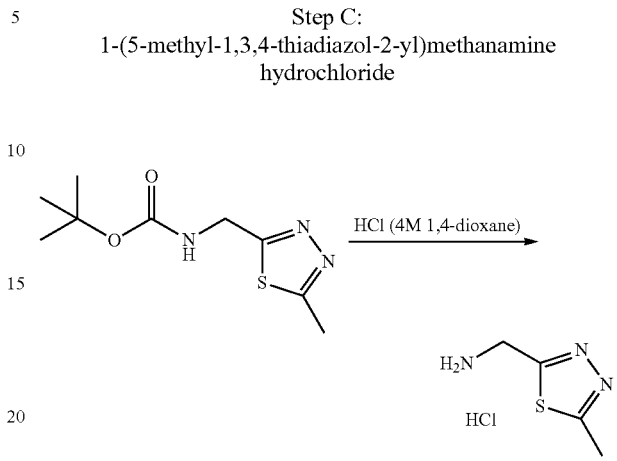

Upon cooling in an ice-water bath, to a 6 mL 4M hydrogen chloride solution in 1,4-dioxane was added the tert-butyl[(5-methyl-1,3,4-thiadiazol-2-yl)methyl]carbamate (391 mg, 1.71 mmol). After the stirring for 1 hr, the reaction mixture was concentrated to give the title compound as white solid (351 mg).

$^1$H-NMR (d$_6$-DMSO, 500 MHz): δ 8.88 (brs, 2H), 4.49 (d, 2H, J=5.5 Hz), 2.74 (s, 3H). LC/MS: m/z=130 (M+H).

Step D: N-[(5-methyl-1,3,4-thiadiazol-2-yl)methyl]-4-(2,4,6-trifluorobenzoyl)-1-H-pyrrole-2-carboxamide

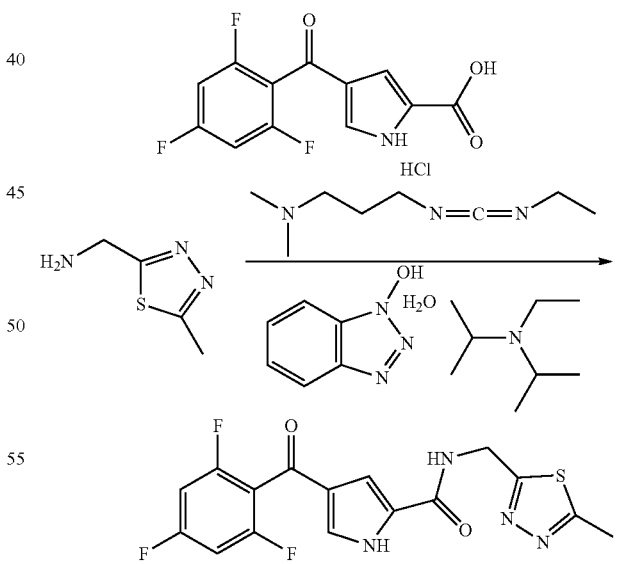

To a DMF 3 mL solution of 4-(2,4,6-trifluorobenzoyl)-1-H-pyrrole-2-carboxylic acid (Intermediate 1) (30 mg, 0.11 mmol), 1-hydroxybenzotriazole hydrate (HOBT) (22 mg, 0.15 mmol) was added N-(3-dimethylaminopropyl)-N'-ethylcarbodiimide-hydrochloride (EDC-hydrochloride)(28 mg, 0.15 mmol). The reaction was stirred for 45 min before 1-(5-methyl-1,3,4-thiadiazol-2-yl)methanamine hydrochloride (19 mg, 0.17 mmol) and diisopropylethylamine (0.1 mL, 0.55 mmol) were added. The reaction mixture was stirred at rt overnight, concentrated and chromatographed on silica gel eluting with AcOEt to give the title compound 29 mg.

$^1$H-NMR (d$_6$-DMSO, 500 MHz): δ 12.6 (brs, 1H), 9.24 (t, 1H, J=6 Hz), 7.52 (s, 1H), 7.25 (s, 1H), 4.74 (d, 2H, J=6 Hz), 2.66 (s, 3H). LC/MS: m/z=381 (M+H), 403 (M+Na).

Example 2 to 20: The title compounds were synthesized following the procedure described for the synthesis of example 1 employing appropriately substituted carbohydrazide instead of acethydrazide.

EXAMPLE 2

N-[(5-butyl-1,3,4-thiadiazol-2-yl)-methyl]-4-(2,4,6-trifluorobenzoyl)-1-H-pyrrole-2-carboxamide

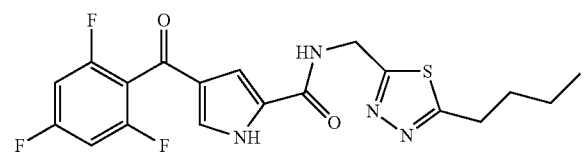 [SMILES: CCCCc1nnc(CNC(=O)c2cc(C(=O)c3c(F)cc(F)cc3F)c[nH]2)s1]

$^1$H-NMR (d$_6$-DMSO, 500 MHz): δ 12.59 (brs, 1H), 9.25 (t, 1H, J=6 Hz), 7.51 (s, 1H), 7.35 (t, 2H, J=8 Hz), 7.25 (s, 1H), 4.75 (d, 2H, J=6 Hz), 2.99 (t, 2H, J=7.6 Hz), 1.65 (p, 2H, J=7.6 Hz), 1.32 (sext., 2H, J=7.6 Hz), 0.87 (t, 3H, J=7.6 Hz).

EXAMPLE 3

N-[(5-isopropyl-1,3,4-thiadiazol-2-yl)methyl]-4-(2,4,6-trifluorobenzoyl)-1-H-pyrrole-2-carboxamide

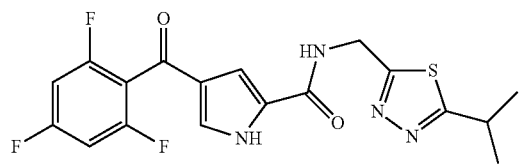 [SMILES: CC(C)c1nnc(CNC(=O)c2cc(C(=O)c3c(F)cc(F)cc3F)c[nH]2)s1]

$^1$H-NMR (d$_6$-DMSO, 500 MHz): δ 12.6 (brs, 1H), 9.25 (t, 1H, J=6 Hz), 7.51 (s, 1H), 7.35 (t, 2H, J=8 Hz), 7.25 (s, 1H), 4.75 (d, 2H, J=6 Hz), 3.35 (m, 1H, J=6.9 Hz), 1.31 (d, 6H, J=6.9 Hz). LC/MS: m/z=409 (M+H).

EXAMPLE 4

N-[(5-cyclopropyl-1,3,4-thiadiazol-2-yl)methyl]-4-(2,4,6-trifluorobenzoyl)-1H-pyrrole-2-carboxamide

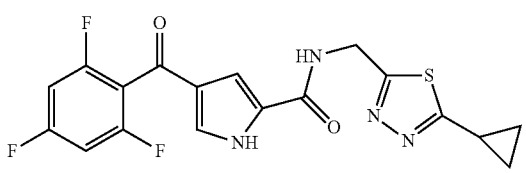 [SMILES: O=C(NCc1nnc(C2CC2)s1)c1cc(C(=O)c2c(F)cc(F)cc2F)c[nH]1]

$^1$H-NMR (d$_6$-DMSO, 500 MHz): δ 12.58 (brs, 1H), 9.225 (t, 1H, J=6 Hz), 7.51 (s, 1H), 7.35 (t, 2H, J=8 Hz), 7.24 (s, 1H), 4.71 (d, 2H, J=6 Hz), 2.46 (m, 1H), 1.16 (m, 2H), 0.955 (m, 2H). LC/MS: m/z=407 (M+H).

EXAMPLE 5

N-[(5-tert-butyl-1,3,4-thiadiazol-2-yl)methyl]-4-(2,4,6-trifluorobenzoyl)-1H-pyrrole-2-carboxamide

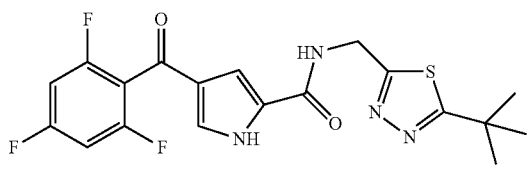 [SMILES: CC(C)(C)c1nnc(CNC(=O)c2cc(C(=O)c3c(F)cc(F)cc3F)c[nH]2)s1]

$^1$H-NMR (d$_6$-DMSO, 500 MHz): δ 12.58 (brs, 1H), 9.257 (t, 1H, J=6 Hz), 7.52 (s, 1H), 7.34 (t, 2H, J=8 Hz), 7.25 (s, 1H), 4.75 (d, 2H, J=6 Hz), 1.37 (s, 9H). LC/MS: m/z=423 (M+H).

EXAMPLE 6

N-[(5-cyclopentyl-1,3,4-thiadiazol-2-yl)methyl]-4-(2,4,6-trifluorobenzoyl)-1H-pyrrole-2-carboxamide

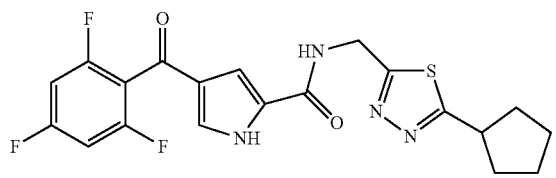 [SMILES: O=C(NCc1nnc(C2CCCC2)s1)c1cc(C(=O)c2c(F)cc(F)cc2F)c[nH]1]

$^1$H-NMR (CDCl$_3$, 500 MHz): δ 10.4 (brs, 1H), 7.6 (brs, 1H), 7.46 (s, 1H), 7.23 (s, 1H), 6.78 (t, 2H, J=8 Hz), 5.0 (d, 2H, J=6.2 Hz), 3.55 (p, 1H, J=7.8 Hz), 2.25 (m, 2H), 1.7-1.9 (m, 6H). LC/MS: m/z=435 (M+H).

EXAMPLE 7

N-[(5-phenyl-1,3,4-thiadiazol-2-yl)methyl]-4-(2,4,6-trifluorobenzoyl)-1H-pyrrole-2-carboxamide

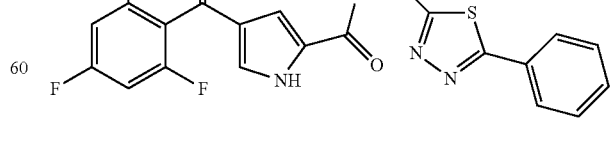

$^1$H-NMR (d$_6$-DMSO, 500 MHz): δ 12.6 (s, 1H), 9.35 (t, 1H, J=6 Hz), 7.96 (m, 2H), 7.54 (t, 2H, J=8 MHz), 4.85 (d, 2H, J=6 Hz). LC/MS: m/z=443 (M+H).

EXAMPLE 8

N-{[5-(4-fluorophenyl)-1,3,4-thiadiazol-2-yl]methyl}-4-(2,4,6-trifluorobenzoyl)-1H-pyrrole-2-carboxamide

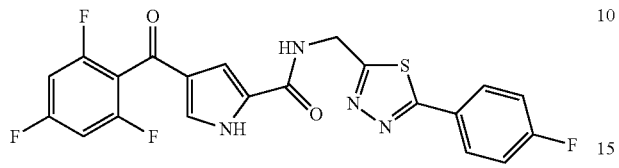

¹H-NMR (d₆-DMSO, 500 MHz): δ 12.7 (s, 1H), 9.35 (t, 1H, J=6 Hz), 8.02 (m, 2H), 7.53 (s, 1H), 7.28 (s, 1H), 4.84 (d, 2H, J=6 Hz). LC/MS: m/z=461 (M+H).

EXAMPLE 9

N {[5-(3-fluorophenyl)-1,3,4-thiadiazol-2-yl]methyl}-4-(2,4,6-trifluorobenzoyl)-1H-pyrrole-2-carboxamide

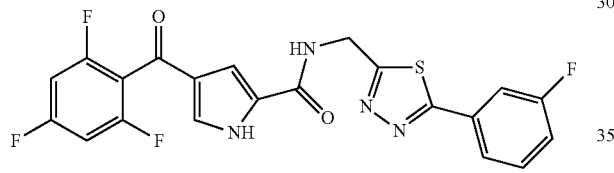

¹H-NMR (d₆-DMSO, 500 MHz): δ 12.6 (s, 1H), 936 (t, 1H, J=6 Hz), 7.80 (d, 2H, J=7 Hz), 7.6-7.5 (m, 2H), 7.4-73 (m, 2H), 7.28 (s, 1H), 4.86 (d, 2H, J=6 Hz). LC/MS: m/z=461 (M+H).

EXAMPLE 10

N-{[5-(4-methoxyphenyl)-1,3,4-thiadiazol-2-yl]methyl}-4-(2,4,6-trifluorobenzoyl)-1H-pyrrole-2-carboxamide

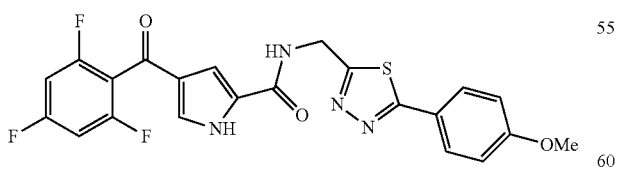

¹H-NMR (d₆-DMSO, 500 MHz): δ 12.6 (s, 1H), 9.32 (t, 1H, J=6 Hz), 7.88 (d, 2H, J=7 Hz), 7.36 (t, 2H, J=8 Hz), 7.28 (s, 1H), 7.07 (d, 2H, J=6 Hz), 4.82 (d, 2H, J=6 Hz), 3.82 (s, 3H). LC/MS: m/z=473 (M+H).

EXAMPLE 11

N-{[5-(2,6-difluorophenyl)-1,3,4-tbiadiazol-2-yl]methyl}-4-(2,4,6-trifluorobenzoyl)-1H-pyrrole-2-carboxamide

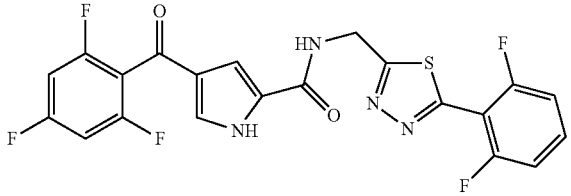 [SMILES: O=C(NCc1nnc(-c2c(F)cccc2F)s1)c1cc(C(=O)c2c(F)cc(F)cc2F)c[nH]1]

LC/MS: m/z=479 (M+H).

EXAMPLE 12

N-[(5-pyridin-2-yl-1,3,4-thiadiazol-2-yl)methyl]-4-(2,4,6-trifluorobenzoyl)-1H-pyrrole-2-carboxamide

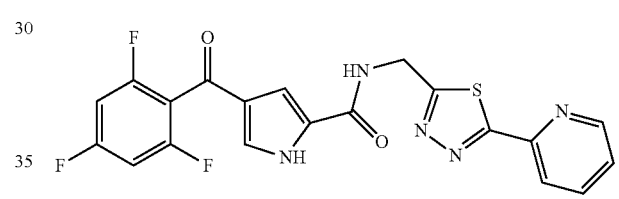

¹H-NMR (d₆-DMSO, 500 MHz): δ 12.6 (s, 1H), 9.33 (t, 1H, J=6 Hz), 8.66 (d, 1H, J=5 Hz), 8.24 (d, 1H, J=8 Hz), 8.02 (t, 1H, J=6 Hz), 7.55 (m, 1H), 7.53 (s, 1H), 7.36 (t, 2H, J=8 Hz), 7.28 (s, 1H), 4.85 (d, 2H, J=6 Hz). LC/MS: m/z=444 (M+H).

EXAMPLE 13

N-[(5-pyridin-3-yl-1,3,4-thiadiazol-2-yl)methyl]-4-(2,4,6-trifluorobenzoyl)-1H-pyrrole-2-carboxamide

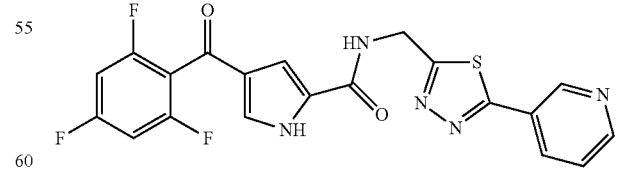

¹H-NMR (d₆-DMSO, 500 MHz): δ 12.6 (s, 1H), 9.37 (t, 2H, J=6 Hz), 9.12 (d, 1H, J=2 Hz), 8.72 (m, 1H), 8.34 (m, 1H), 7.55 (m, 1H), 7.53 (s, 1H), 7.36 (t, 2H, J=8 Hz), 7.29 (s 1H), 4.87 (d, 2H, J=6 Hz). LC/MS: m/z=444 (M+H).

EXAMPLE 14

N-{[5-(1H-pyrrol-2-yl)-1,3,4-thiadiazol-2-yl]methyl}-4-(2,4,6-trifluorobenzoyl)-1H-pyrrole-2-carboxamide

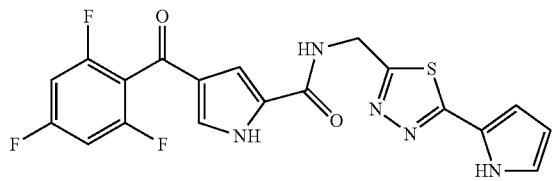 [SMILES: O=C(NCc1nnc(-c2ccc[nH]2)s1)c1cc(C(=O)c2c(F)cc(F)cc2F)c[nH]1]

¹H-NMR (d₆-DMSO, 500 MHz): δ 12.6 (brs, 1H), 12.0 (s, 1H), 9.3 (t, 1H, J=6 Hz), 7.53 (s, 1H), 7.35 (t, 2H, J=8 Hz), 7.27 (s, 1H), 6.98 (m, 1H), 6.71 (m, 1H), 6.19 (m, 1H), 4.8 (d, 2H, J=6 Hz). LC/MS: m/z=432 (M+H).

EXAMPLE 15

N-{[5-(2-furyl)-1,3,4-thiadiazol-2-yl]methyl}-4-(2,4,6-trifluorobenzoyl)-1H-pyrrole-2-carboxamide

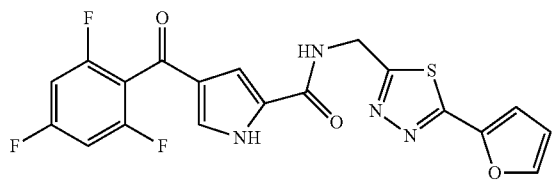 [SMILES: O=C(NCc1nnc(-c2ccco2)s1)c1cc(C(=O)c2c(F)cc(F)cc2F)c[nH]1]

¹H-NMR (CD₃OD, 500 MHz): δ 7.77 (d, 1H, J=1.4 Hz), 7.5 (s, 1H), 7.24 (d, 1H, J=1.4 Hz), 7.22 (d, 1H, J=3.4 Hz), 7.025 (t, 2H, J=8 Hz), 6.68 (dd, 1H, J=1.4 Hz), 4.92 (s, 2H), 4.59 (brs, 1H). LC/MS: m/z=433 (M+H).

EXAMPLE 16

N-{[5-(2-ethoxypyridin-3-yl)-1,3,4-thiadiazol-2-yl]methyl}-4-(2,4,6-trifluorobenzoyl)-1H-pyrrole-2-carboxamide

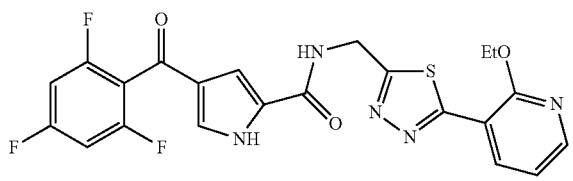 [SMILES: CCOc1ncccc1-c1nnc(CNC(=O)c2cc(C(=O)c3c(F)cc(F)cc3F)c[nH]2)s1]

¹H-NMR (d₆-DMSO, 500 MHz): δ 12.6 (s, 1H), 9.29 (t, 2H, J=6 Hz), 8.63 (dd, 1H, J=2 Hz, 8Hz), 8.36 (dd, 1H, J=-2 Hz, 5 Hz), 7.52 (d, 1H, J=2 Hz), 7.25 (m, 2H), 7.20 (s, 1H), 7.18 (m, 1H), 4.86 (d, 2H, J=6 Hz), 4.51 (q, 2H, J=7 Hz), 1.39 (t, 3H, J=7 Hz). LC/MS: m/z=488 (M+H).

EXAMPLE 17

N-{[5-(6-methoxypyridin-3-yl)-1,3,4-thiadiazol-2-yl]methyl}-4-(2,4,6-trifluorobenzoyl)-1H-pyrrole-2-carboxamide

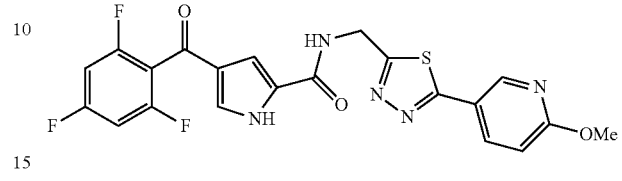

¹H-NMR (d₆-DMSO, 500 MHz): δ 12.6 (s, 1H), 9.35 (t, 1H, J=6 Hz), 8.73 (d, 1H, J=2 Hz), 8.25 (dd, 1H, J=2 Hz, 9 Hz), 7.53 (d, 1H, J=2 Hz), 7.36 (d, 2H, J=8 Hz), 7.28 (s, 1H), 6.97 (d, 1H, 9 Hz), 4.85 (d, 2H, J=6 Hz), 3.92 (s, 3H). LC/MS: m/z=474 (M+H).

EXAMPLE 18

N-{[5-(6-methoxypyridin-2-yl)-1,3,4-thiadiazol-2-yl]methyl}-4-(2,4,6-trifluorobenzoyl)-1H-pyrrole-2-carboxamide

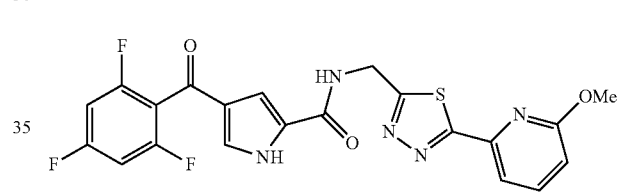

¹H-NMR (d₆-DMSO, 500 MHz): δ 12.6 (s, 1H), 9.34 (t, 1H, J=6 Hz), 7.91 (t, 1H, J=8 Hz), 7.84 (d, 1H, J=7 Hz), 7.54 (s, 1H), 7.36 (t, 2H, J=6 Hz), 7.28 (s, 1H), 7.00 (d, 1H, J=7 Hz), 4.84 (d, 2H, J=6 Hz), 3.89 (s, 3H). LC/MS: m/z=474 (M+H).

EXAMPLE 19

N-{[5-(2-methoxypyridin-4-yl)-1,3,4-thiadiazol-2-yl]methyl}-4-(2,4,6-trifluorobenzoyl)-1H-pyrrole-2-carboxamide

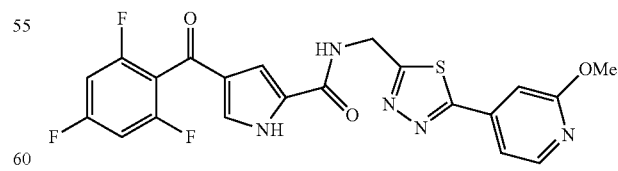

¹H-NMR (d₆-DMSO, 500 MHz): δ 12.6 (s, 1H), 9.38 (t, 1H, J=6 Hz), 8.32 (t, 1H, J=6 Hz), 7.52 (m, 2H), 7.36 (t, 2H, J=8 Hz), 7.32 (s, 1H), 7.29 (s, 1H), 4.87 (d, 2H, J=6 Hz), 3.90 (s, 3H).

LC/MS: m/z=474 (M+H).

EXAMPLE 20

N-{[5-(3-methyl-1H-pyrazol-5-yl)-1,3,4-thiadiazol-2-yl]methyl}-4-(2,4,6-trifluorobenzoyl)-1H-pyrrole-2-carboxamide

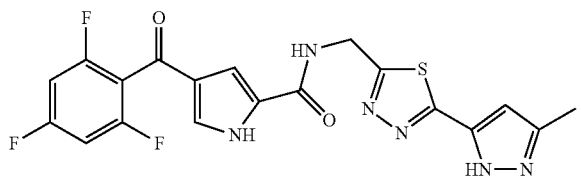 [SMILES: Cc1cc(-c2nnc(CNC(=O)c3cc(C(=O)c4c(F)cc(F)cc4F)c[nH]3)s2)[nH]n1]

¹H-NMR (d₆-DMSO, 500 MHz): δ 13.1 (s, 1H), 12.6 (brs, 1H), 9.3 (t, 1H, J=6 Hz), 7.53 (s, 1H), 7.33 (t, 2H, J=8 Hz), 7.27 (s, 1H), 6.59 (s, 1H), 4.8 (d, 2H, J=6 Hz), 2.28 (s, 3H). LC/MS: m/z=447 (M+H).

EXAMPLE 21

N-[(5-pyrazin-2-yl-1,3,4-thiadiazol-2-yl)methyl]-4-(2,4,6-trifluorobenzoyl)-1H-pyrrole-2-carboxamide

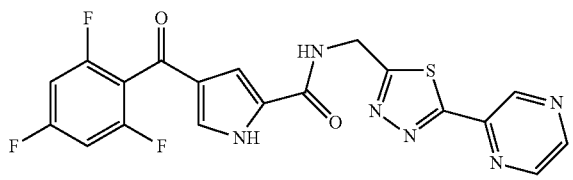 [SMILES: O=C(NCc1nnc(-c2cnccn2)s1)c1cc(C(=O)c2c(F)cc(F)cc2F)c[nH]1]

Step A: tert-butyl {2-oxo-2-[2-(pyrazin-2-ylcarbonyl)hydrazino]ethyl}carbamate

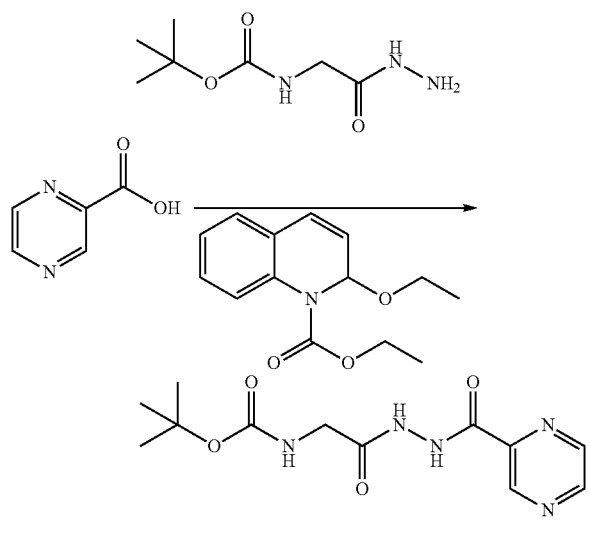

Under N₂ atmosphere, to a dichloromethane 5 mL solution of pyrazine-2-carboxylic acid (328 mg, 2.64 mmol) was added EEDQ (653 mg, 2.64 mmol). After stirring for 45 min, to it was added N-(tert-butyloxycarbonyl)glycylhydrazide (500 mg, 2.64 mmol). Stirring continued at rt overnight. The reaction mixture was concentrated and triturated from dichloromethane to give the title compound (666 mg).

Step B-D: Following the procedure described in example 1 step B-D, title compound was prepared.

¹H-NMR (d₆-DMSO, 500 MHz): δ 12.6 (s, 1H), 9.44 (s, 1H), 9.38 (t, 2H, J=6 Hz), 8.82 (s, 1H), 8.78 (s, 1H), 7.54 (s, 1H), 7.36 (t, 2H, J=8 Hz), 7.28 (s, 1H), 4.88 (d, 2H, J=6 Hz). LC/MS: m/z=445 (M+H).

Title compounds in examples 22-31 were prepared following the procedure described in example 21 employing appropriately substituted carboxylic acids.

EXAMPLE 22

N-[(5-cyclobutyl-1,3,4-thiadiazol-2-yl)methyl]-4-(2,4,6-trifluorobenzoyl)-1H-pyrrole-2-carboxamide

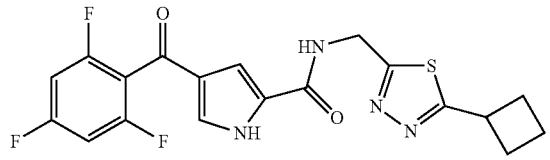 [SMILES: O=C(NCc1nnc(C2CCC2)s1)c1cc(C(=O)c2c(F)cc(F)cc2F)c[nH]1]

¹H-NMR (d₆-DMSO, 500 MHz): δ 12.59 (s, 1H), 9.25 (t, 1H, J=6 Hz), 7.516 (s, 1H), 7.35 (t, 2H, J=8 Hz), 7.25 (s, 1H), 4.75 (d, 2H, J=6 Hz), 3.93 (p, 1H, J=8.5 Hz), 2.4 (m, 2H), 2.234 (pd, 2H, J=9.2 Hz, J=2.4 Hz), 2.015 (sext., 1H, J=9 Hz), 1.89 (m, 1H). LC/MS: m/z=421 (M+H).

EXAMPLE 23

N-{[5-(1-methylcyclopropyl)-1,3,4-thiadiazol-2-yl]methyl}-4-(2,4,6-trifluorobenzoyl)-1H-pyrrole-2-carboxamide

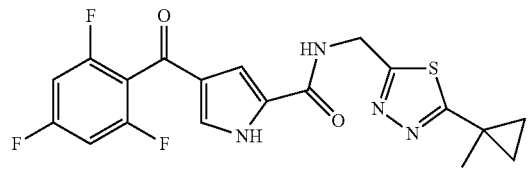 [SMILES: CC1(c2nnc(CNC(=O)c3cc(C(=O)c4c(F)cc(F)cc4F)c[nH]3)s2)CC1]

¹H-NMR (d₆-DMSO, 500 MHz): δ 12.57 (brs, 1H), 9.24 (t, 1H, J=6 Hz), 7.51 (s, 1H), 7.34 (t, 2H, J=8 Hz), 7.24 (s, 1H), 4.72 (d, 2H, J=6 Hz), 1.49 (s, 3H), 1.15 (m, 2H), 1.04 (m, 2H). LC/MS: m/z=421 (M+H).

EXAMPLE 24

N-[(5-sec-butyl-1,3,4-thiadiazol-2-yl)methyl]-4-(2,4,6-trifluorobenzoyl)-1H-pyrrole-2-carboxamide

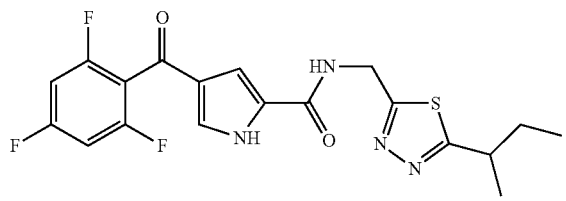 [SMILES: CCC(C)c1nnc(CNC(=O)c2cc(C(=O)c3c(F)cc(F)cc3F)c[nH]2)s1]

¹H-NMR (d₆-DMSO, 500 MHz): δ 12.59 (s, 1H), 9.26 (t, 1H, J=6 Hz), 7.52 (s, 1H), 7.35 (t, 2H, J=8 Hz), 7.26 (s, 1H), 4.76 (d, 2H, J=6 Hz), 3.195 (qt, 1H, J=6.9, 6.8 Hz), 1.66 (m, 2H, J=7.4, 6.8 Hz), 1.29 (d, 3H, J=6.9 Hz), 0.833 (t, 3H, J=7.4 Hz). LC/MS: m/z=423 (M+H).

EXAMPLE 25

N-{[5-(3-isopropyl-1H-pyrazol-5-yl)-1,3,4-thiadiazol-2-yl]methyl}-4-(2,4,6-trifluorobenzoyl)-1H-pyrrole-2-carboxamide

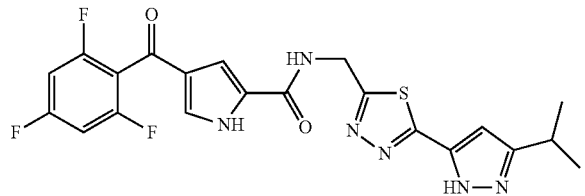 [SMILES: CC(C)c1cc(-c2nnc(CNC(=O)c3cc(C(=O)c4c(F)cc(F)cc4F)c[nH]3)s2)[nH]n1]

$^1$H-NMR (d$_6$-DMSO, 500 MHz): δ 13.16 (s, 1H), 12.61 (s, 1H), 9.29 (t, 1H, J=6 Hz), 7.52 (s, 1H), 7.34 (t, 2H, J=8 Hz), 7.26 (s, 1H), 6.61 (s, 1H), 4.8 (d, 2H, J=6 Hz), 3.08 (sept, 1H, J=6.9 Hz), 1.24 (d, 6H, J=6.9 Hz). LC/MS: m/z=475 (M+H).

EXAMPLE 26

N-{[5-(3-isobutyl-1H-pyrazol-5-yl)-1,3,4-thiadiazol-2-yl]methyl}-4-(2,4,6-trifluorobenzoyl)-1H-pyrrole-2-carboxamide

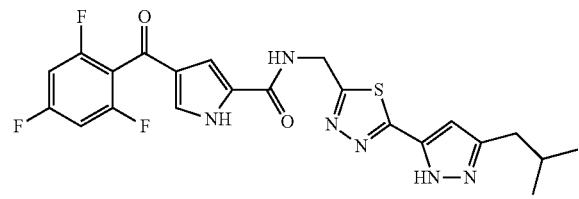 [SMILES: CC(C)Cc1cc(-c2nnc(CNC(=O)c3cc(C(=O)c4c(F)cc(F)cc4F)c[nH]3)s2)[nH]n1]

$^1$H-NMR (d$_6$-DMSO, 500 MHz): δ12.6 (s, 1H), 9.29 (t, 1H, J=6 Hz), 7.52 (s, 1H), 7.34 (t, 2H, J=8 Hz), 7.26 (s, 1H), 6.6 (s, 1H), 4.8 (d, 2H, J=6 Hz), 2.51 (d, 2H, J=7.1 Hz), 1.91 (m, 1H, J=6.8 Hz, J=7.1 Hz), 0.88 (d, 6H, J=6.8 Hz). LC/MS: m/z=489 (M+H).

EXAMPLE 27

4-(2,4,6-trifluorobenzoyl)-N-({5-[3-(trifluoromethyl)-1H-pyrazol-5-yl]-1,3,4-thiadiazol-2-yl}methyl)-1H-pyrrole-2-carboxamide

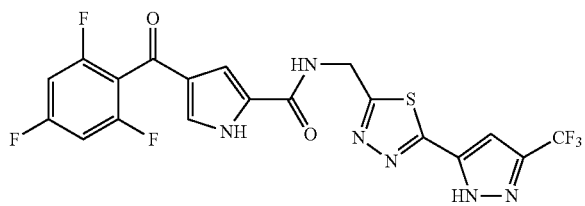 [SMILES: O=C(NCc1nnc(-c2cc(C(F)(F)F)n[nH]2)s1)c1cc(C(=O)c2c(F)cc(F)cc2F)c[nH]1]

$^1$H-NMR (d$_6$-DMSO, 500 MHz): δ 12.62 (s, 1H), 939 (t, 1H, J=5.8), 7.54 (s, 1H), 7.47 (s, 1H), 7.35 (t, 2H, J=8 Hz), 7.285 (s, 1H), 4.87 (d, 2H, J=5.8 Hz). LC/MS: m/z=501 (M+H).

EXAMPLE 28

N-{[5-(1H-indazol-3-yl)-1,3,4-thiadiazol-2-yl]methyl}-4-(2,4,6-trifluorobenzoyl)-1H-pyrrole-2-carboxamide

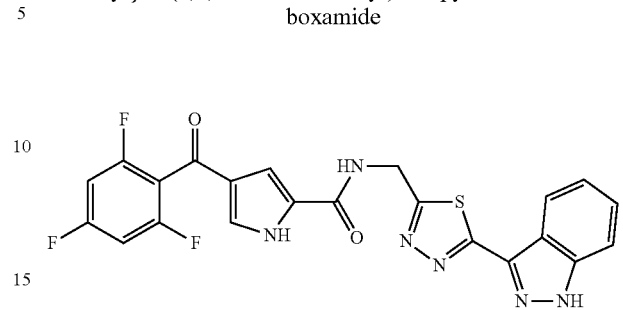

$^1$H-NMR (d$_6$-DMSO, 500 MHz): δ 12.62 (s, 1H), 9.35 (t, 1H, J=6 Hz), 8.31 (d, 1H, J=8.3 Hz), 7.66 (d, 1H, J=8.3 Hz), 7.54 (s, 1H), 7.49 (t, 1H, J=7.4 Hz), 7.35 (m, 3H), 7.29 (s, 1H), 4.87 (d, 2H, J=6 Hz). LC/MS: m/z=483 (M+H).

EXAMPLE 29

N-[(5-pyrazolo[1,5-c]pyrimidin-2-yl-1,3,4-thiadiazol-2-yl)methyl]-4-(2,4,6-trifluorobenzoyl)-1H-pyrrole-2-carboxamide

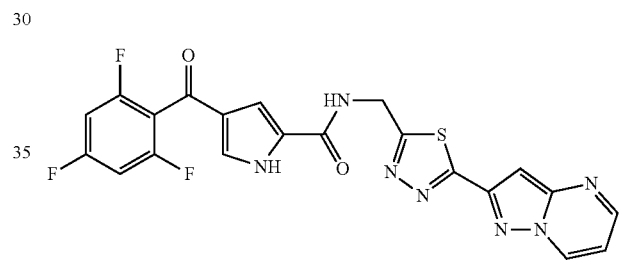

$^1$H-NMR (d$_6$-DMSO, 500 MHz): δ 12.62 (s, 1H), 9.36 (t, 1H, J=6 Hz), 9.17 (d, 1H, J=7 Hz), 8.65 (d, 1H, J=4 Hz), 7.53 (s, 1H), 7.342 (t, 2H, J=8 Hz), 7.32 (s, 1H), 7.28 (s, 1H), 7.176 (dd, 1H, J=7 Hz, J=4 Hz), 4.88 (d, 2H, J=6 Hz). LC/MS: m/z=484 (M+H).

EXAMPLE 30

N-{[5-(1,2,3-thiadiazol-4-yl)-1,3,4-thiadiazol-2-yl]methyl}-4-(2,4,6-trifluorobenzoyl)-1H-pyrrole-2-carboxamide

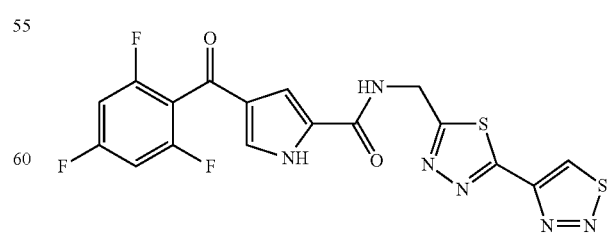

$^1$H-NMR (d$_6$-DMSO, 500 MHz): δ 12.62 (s, 1H), 9.93 (s, 1H), 9.4 (t, 1H, J=6 Hz), 7.53 (s, 1H), 7.34 (t, 2H, J=8 Hz), 7.27 (s, 1H), 4.89 (d, 2H, J=6 Hz). LC/MS: m/z=451 (M+H).

EXAMPLE 31

N-{[5-(2,4,5,6-tetrahydrocyclopenta[c]pyrazol-3-yl)-1,3,4-thiadiazol-2-yl]methyl}-4-(2,4,6-trifluorobenzoyl)-1H-pyrrole-2-carboxamide

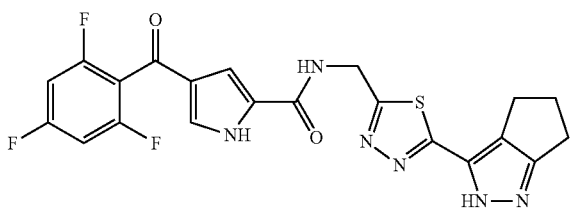 [SMILES: O=C(NCc1nnc(-c2[nH]nc3c2CCC3)s1)c1cc(C(=O)c2c(F)cc(F)cc2F)c[nH]1]

$^1$H-NMR (d$_6$-DMSO, 500 MHz): δ 12.99 (brs, 1H), 12.62 (s, 1H), 9.29 (t, 1H, J=6 Hz), 7.53 (s, 1H), 7343 (t, 2H, J=8 Hz), 7.27 (s, 1H), 4.8 (d, 2H, J=6 Hz), 273 (m, 4H), 2.53 (m, 2H). LC/MS: m/z=473 (M+H).

EXAMPLE 32

N-{[5-(1H-pyrazol-5-yl)-1,3,4-thiadiazol-2-yl]methyl}-4-(2,4,6-trifluorobenzoyl)-1H-pyrrole-2-carboxamide

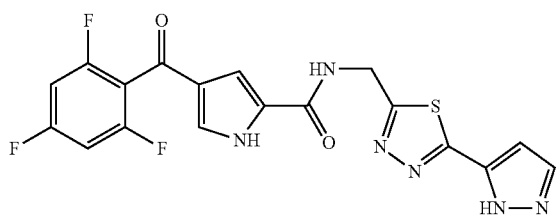 [SMILES: O=C(NCc1nnc(-c2ccn[nH]2)s1)c1cc(C(=O)c2c(F)cc(F)cc2F)c[nH]1]

Step A: N'-(2-chloroacetyl)-1H-pyrazole-5-carbohydrazide

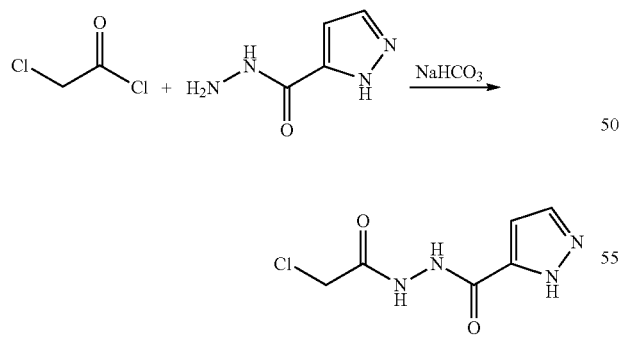

To a suspension of 1H-pyrazole-5-carbohydrazide (102 mg, 0.81 mmol) in 7 mL AcOEt was added 1.8 mL of 1M sodium bicarbonate solution and the initial white suspension was stirred for a few minutes until it became completely clear two-phase solution. Upon cooling in an ice-water bath to it was added 0.7 ml AcOEt solution of chloroacetyl chloride (110 mg, 0.97 mmol). After stirring overnight, the reaction mixture was poured into a separatory funnel. The organic layer was separated and the aqueous layer was extracted twice with AcOEt. The combined org layers were dried over anhydrous sodium sulfate, filtered and concentrated to give a white solid (110 mg).

$^1$H-NMR (d$_6$-DMSO, 500 MHz): δ 13.4 (s, 1H), 10.2 (s, 1H), 10.1 (s, 1H), 7.86 (s, 1H), 6.71 (s, 1H), 4.17 (s, 2H).

Step B: 2-(chloromethyl)-5-(1H-pyrazol-5-yl)-1,3,4-thiadiazole

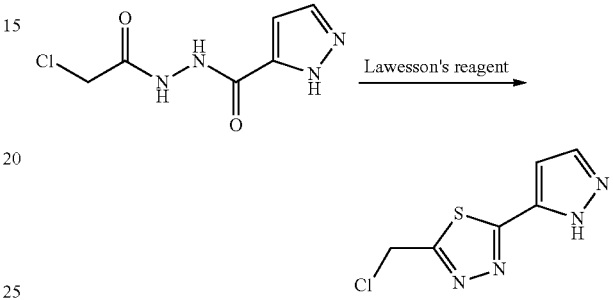

N'-(2-chloroacetyl)-1H-pyrazole-5-carbohydrazide (110 mg, 0.54 mmol) and Lawesson's reagent (220 mg, 0.54 mmol) were suspended in THF 5.5 mL and then heated to reflux for 3 hr. The reaction mixture was concentrated and chromatographed on silica gel eluting with a gradient solvent mixture of AcOEt and hexanes to give the title compound as white solid (60.5 mg).

$^1$H-NMR (d$_6$-DMSO, 500 MHz): δ 7.97 (s, 1H), 6.91 (s, 1H), 5.26 (s, 2H).

Step C: 2-(azidomethyl)-5-(1H-pyrazol-5-yl)-1,3,4-thiadiazole

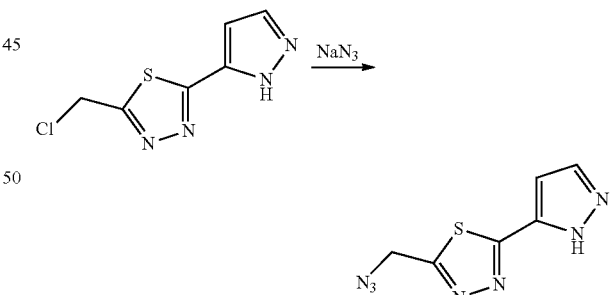

To a 1 mL DMF solution of 2-(chloromethyl)-5-(1H-pyrazol-5-yl)-1,3,4-thiadiazole (58 mg, 0.29 mmol) was added sodium azide (20 mg, 0.30 mmol). Stirring continued at rt for 3 hr. The reaction mixture was concentrated and diluted with AcOEt and water. The organic layer was separated. The aqueous layer was extracted with AcOEt twice and the combined organic layers were dried over anhydrous sodium sulfate, filtered, and concentrated to give the title compound (60 mg).

$^1$H-NMR (d$_6$-DMSO, 500 MHz): δ 13.5 (s, 1H), 7.97 (s, 1H), 6.90 (s, 1H), 5.00 (s, 2H).

Step D: 1-[5-(1H-pyrazol-5-yl)-1,3,4-thiadiazol-2-yl]methanamine

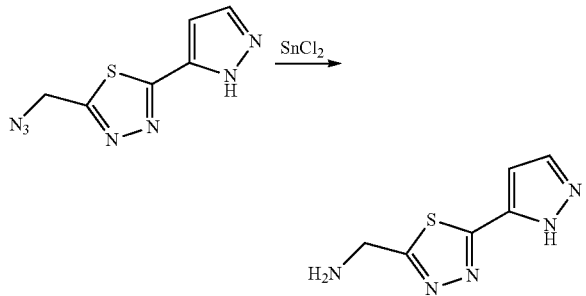

To a 3 mL methanol solution of 2-(azidomethyl)-5-(1H-pyrazol-5-yl)-1,3,4-thiadiazole (50 mg, 0.24 mmol) was added Tin (II) chloride, anhydrous (82 mg. 0.43 mmol) and the resulting yellow solution was stirred at rt overnight. The reaction mixture was concentrated and purified by HPLC (acetonitrile-water-ammonium hydroxide eluent) to give the title compound (37 mg).

$^1$H-NMR (d$_6$-DMSO, 500 MHz): δ 13.4 (s, 1H), 7.92 (s, 1H), 6.84 (s, 1H), 4.12 (s, 2H).

Step E: N-{[5-(1H-pyrazol-5-yl)-1,3,4-thiadiazol-2-yl]methyl}-4-(2,4,6-trifluorobenzoyl)-1H-pyrrole-2-carboxamide Following the procedure of example 1, step D, the title compound was prepared.

$^1$H-NMR (d$_6$-DMSO, 500 MHz): δ 13.48 (s, 1H), 12.64 (s, 1H), 9.35 (t, 1H, J=5.7 Hz), 7.93 (s, 1H), 7.53 (s, 1H), 7.35 (t, 2H, J=8 Hz), 7.28 (s, 1H), 6.86 (s, 1H), 4.81 (d, 2H, J=5.7 Hz). LC/MS: m/z=433 (M+H).

The title compounds in examples 33-34 were synthesized following the procedure described for example 32 employing appropriately substituted carbohydrazides.

EXAMPLE 33

N-{[5-(1,5-dimethyl-1H-pyrazol-3-yl)-1,3,4-thiadiazol-2-yl]methyl}-4-(2,4,6-trifluorobenzoyl)-1H-pyrrole-2-carboxamide

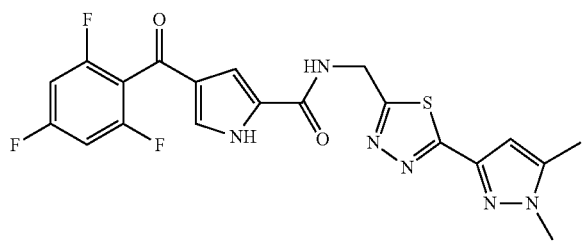 [SMILES: Cc1cc(-c2nnc(CNC(=O)c3cc(C(=O)c4c(F)cc(F)cc4F)c[nH]3)s2)nn1C]

$^1$H-NMR (d$_6$-DMSO, 500 MHz): δ 12.6 (brs, 1H), 9.29 (t, 1H, J=6 Hz), 7.54 (s, 1H), 7.36 (t, 2H, J=8 Hz), 7.27 (s, 1H), 6.65 (s, 1H), 4.8 (d, 2H, J=6 Hz), 3.78 (s, 3H), 2.31 (s, 3H). LC/MS: m/z 461 (M+H).

EXAMPLE 34

N-{[5-(2H-1,2,3-triazol-4-yl)-1,3,4-thiadiazol-2-yl]methyl}-4-(2,4,6-trifluorobenzoyl)-1,1-pyrrole-2-carboxamide

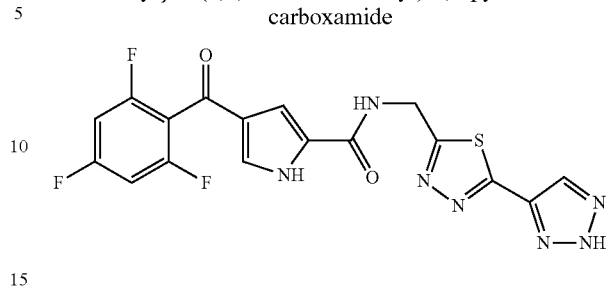

$^1$H-NMR (d$_6$-DMSO, 500 MHz): δ 12.64 (s, 1H), 9.34 (t, 1H, J=5.4 Hz), 8.87 (brs, 1H), 8.42 (brs, 1H), 7.54 (s, 1H), 7.36 (t, 2H, J=8 Hz), 7.28 (s, 1H), 4.85 (d, 2H, J=5.4 Hz). LC/MS: m/z=434 (M+H).

EXAMPLE 35

N-{[5-(2-oxo-1,2-dihydropyridin-3-yl)-1,3,4-thiadiazol-2-yl]methyl}-4-(2,4,6-trifluorobenzoyl)-1H-pyrrole-2-carboxamide

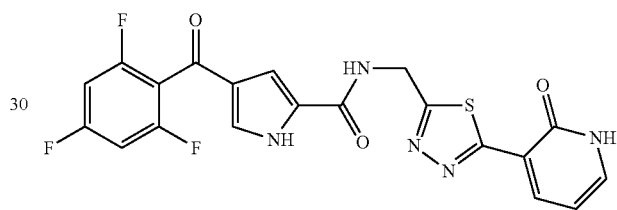

To N-{[5-(2-ethoxypyridin-3-yl)-1,3,4-thiadiazol-2-yl]methyl}-4-(2,4,6-trifluorobenzoyl)-1H-pyrrole-2-carboxamide (example 16) (102 mg, 021 mmol) was added 3 mL of 4M hydrogen chloride in 1,4-dioxane and the resulting suspension was stirred at rt for 7 hr. The reaction mixture was concentrated. The residue was triturated from dichloromethane to give the title compound (95 mg).

$^1$H-NMR (d$_6$-DMSO, 500 MHz): δ 12.6 (s, 1H), 9.28 (t, 1H, J=6 Hz), 8.60 (dd, 1H, J=2 Hz, 8 Hz), 7.73 (s, 1H), 7.52 (s, 1H), 7.35 (t, 2H, J=2 Hz, 8 Hz), 7.27 (s, 1H), 6.52 (t, 1H, J=7 Hz), 4.82 (d, 2H, J=6 Hz). LC/MS: m/z=460 (M+H).

EXAMPLE 36

N-{[5-(6-oxo-1,6-dihydropyridin-3-yl)-1,3,4-thiadiazol-2-yl]methyl}-4-(2,4,6-trifluorobenzoyl)-1H-pyrrole-2-carboxamide

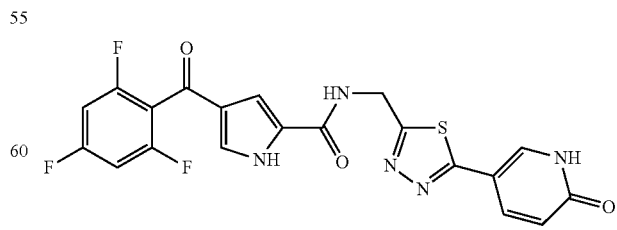

Following the procedure described in example 35 except that the reaction mixture was heated at 70° C. for 6 hr, the title compound was prepared employing N-{[5-(6-methoxypyridin-3-yl)-1,3,4-thiadiazol-2-yl]methyl}-4-(2,4,6-trifluorobenzoyl)-1H-pyrrole-2-carboxamide (example 17) as the starting material.

¹H-NMR (d₆-DMSO, 500 MHz): δ 12.6 (s, 1H), 9.32 (t, 1H, J=6 Hz), 8.06 (d, 1H, J=3 Hz), 7.97 (dd, 1H, J=3 Hz, 10 Hz), 7.52 (s, 1H), 7.35 (t, 2H, J=8 Hz), 7.27 (s, 1H), 6.45 (d, 1H, J=10 Hz), 4.79 (d, 2H, J=6 Hz). LC/MS: m/z=460 (M+H).

EXAMPLE 37

N-{[5-(6-oxo-1,6-dihydropyridin-2-yl)-1,3,4-thiadiazol-2-yl]methyl}-4-(2,4,6-trifluorobenzoyl)-1H-pyrrole-2-carboxamide

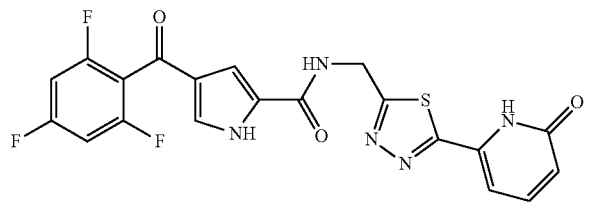 [SMILES: O=C(NCc1nnc(-c2cccc(=O)[nH]2)s1)c1cc(C(=O)c2c(F)cc(F)cc2F)c[nH]1]

Following the procedure described in example 35 except that the reaction mixture was heated at 100° C. for 6 hr, the title compound was prepared employing N-{[5-(6-methoxypyridin-2-yl)-1,3,4-thiadiazol-2-yl]methyl}-4-(2,4,6-trifluorobenzoyl)-1H-pyrrole-2-carboxamide (example 18) as the starting material.

¹H-NMR (d₆-DMSO, 500 MHz): δ 12.6 (s, 1H), 11.2 (brs, 1H), 9.35 (t, 1H, J=6 Hz), 7.81 (t, 1H, J=7 Hz), 7.69 (s, 1H), 7.54 (d, 1H, J=2 Hz), 7.36 (t, 2H, J=8 Hz), 7.28 (s, 1H), 6.79 (d, 1H, J=8 Hz), 4.82 (d, 2H, J=6 Hz). LC/MS: m/z=460 (M+H).

EXAMPLE 38

N-{[5-(2-oxo-1,2-dihydropyridin-4-yl)-1,3,4-thiadiazol-2-yl]methyl}-4-(2,4,6-trifluorobenzoyl)-1H-pyrrole-2-carboxamide

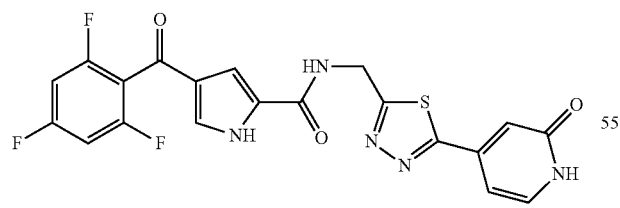

Following the procedure described in example 35 except that the reaction mixture was heated at 100° C. for 6 hr, the title compound was prepared employing N-{[5-(2-methoxypyridin-4-yl)-1,3,4-thiadiazol-2-yl]methyl}-4-(2,4,6-trifluorobenzoyl)-1H-pyrrole-2-carboxamide (example 19) as the starting material.

LC/MS: m/z=460 (M+H).

EXAMPLE 39

4-(2,4-difluorobenzoyl)-N-[(5-methyl-1,3,4-thiadiazol-2-yl)methyl]-1H-pyrrole-2-carboxamide

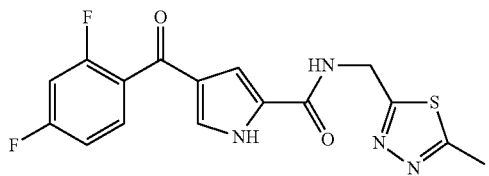 [SMILES: Cc1nnc(CNC(=O)c2cc(C(=O)c3ccc(F)cc3F)c[nH]2)s1]

The title compound was prepared following the procedure described in example 1 employing intermediate 3 instead of intermediate 1.

¹H-NMR (CDCl₃, 500 MHz): δ 7.93 (s, 1H), 7.73 (t, 1H, J=7 Hz), 6.86 (d, 1H, J=8 Hz), 5.33 (brs, 1H), 4.78 (d, 2H, J=6 Hz), 4.00 (s, 3H). LC/MS: m/z=363 (M+H).

EXAMPLE 40

4-(2,6-difluorobenzoyl)-N-[(5-methyl-1,3,4-thiadiazol-2-yl)methyl]-1H-pyrrole-2-carboxamide

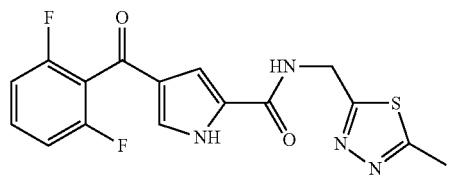 [SMILES: Cc1nnc(CNC(=O)c2cc(C(=O)c3c(F)cccc3F)c[nH]2)s1]

The title compound was prepared following the procedure described in example 1 employing intermediate 2 instead of intermediate 1.

¹H-NMR (CDCl₃, 500 MHz): δ 10.7 (s, 1H), 7.88 (t, 1H, J=6 Hz), 7.01 (m, 2H), 5.00 (d, 2H, J=6 Hz), 2.77 (s, 3H). LC/MS: m/z=363 (M+H).

EXAMPLE 41

4-(2,6-difluorobenzoyl)-N-{[5-(1H-pyrazol-5-yl)-1,3,4-thiadiazol-2-yl]methyl}-1H-pyrrole-2-carboxamide

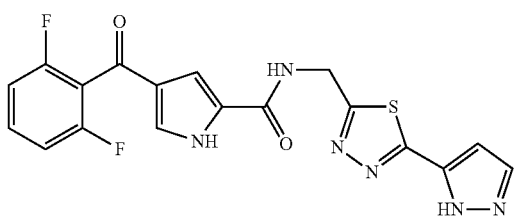 [SMILES: O=C(NCc1nnc(-c2ccn[nH]2)s1)c1cc(C(=O)c2c(F)cccc2F)c[nH]1]

The title compound was prepared following the procedure described in example 32 employing intermediate 2 instead of intermediate 1.

¹H-NMR (500 MHz, d⁶-DMSO): δ 13.47 (bs, 1H), 12.60 (bs, 1H), 9.32 (m, 1H), 7.93 (m, 1H), 7.61 (m, 1H), 7.45 (s, 1H), 7.25 (m, 3H), 6.86 (s, 1H), 4.81 (s, 2H). LC/MS: m/z=415 (M+H).

EXAMPLE 42

4-(2,6-difluoro-4-methylbenzoyl)-N-{[5-(1H-pyrazol-5-yl)-1,3,4-thiadiazol-2-yl]methyl}-1-pyrrole-2-carboxamide

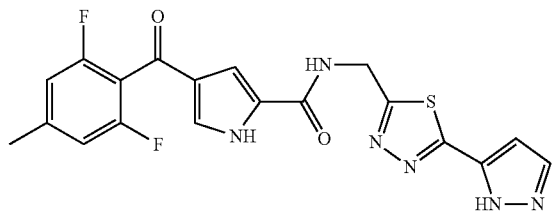 [SMILES: Cc1cc(F)c(C(=O)c2c[nH]c(C(=O)NCc3nnc(-c4ccn[nH]4)s3)c2)c(F)c1]

The title compound was prepared following the procedure described in example 32 employing intermediate 4 instead of intermediate 1.

$^1$H-NMR (500 MHz, d$^6$-DMSO): δ 13.45 (bs, 1H), 12.58 (bs, 1H), 9.30 (m, 1H), 7.94 (s, 1H), 7.43 (s, 1H), 7.23 (s, 1H), 7.08 (m, 2H), 6.86 (s, 1H), 4.81 (s, 2H), 2.37 (s, 3H). LC/MS: m/z=429 (M+H).

EXAMPLE 43

N-{[5-(2-oxo-1,2-dihydropyridin-3-yl)-1,3,4-thiadiazol-2-yl]methyl}-4-(2,4,6-trifluorobenzyl)-1H-pyrrole-2-carboxamide

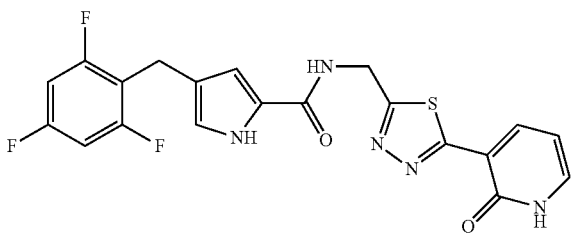 [SMILES: O=C(NCc1nnc(-c2ccc[nH]c2=O)s1)c1cc(Cc2c(F)cc(F)cc2F)c[nH]1]

The title compound was prepared following the procedure described in example 35 employing intermediate 5 instead of intermediate 1.

$^1$H-NMR (d$_6$-DMSO, 500 MHz): δ 12.6 (s, 1H), 11.4 (s, 1H), 8.90 (t, 1H, J=6 Hz), 8.58 (dd, 1H, J=2 Hz, 7 Hz), 7.72 (m, 1H), 7.15 (t, 1H, J=8 Hz), 6.70 (s, 1H), 6.62 (s, 1H), 6.50 (t, 1H, J=6 Hz), 4.74 (d, 2H, J=6 Hz), 3.71 (s, 2H).

EXAMPLE 44

N-[(5-pyridin-2-yl-1,3,4-thiadiazol-2-yl)methyl]-4-(2,4,6-trifluorobenzyl)-1H-pyrrole-2-carboxamide

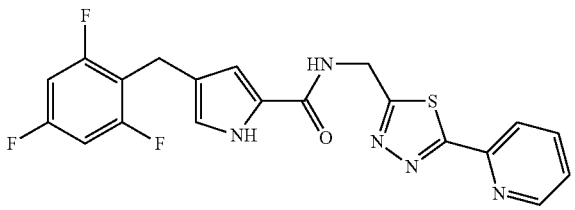 [SMILES: O=C(NCc1nnc(-c2ccccn2)s1)c1cc(Cc2c(F)cc(F)cc2F)c[nH]1]

The title compound was prepared following the procedure described in example 12 employing intermediate 5 instead of intermediate 1.

$^1$H-NMR (CDCl$_3$, 500 MHz): δ 9.22 (s, 1H), 8.64 (d, 1H, J=5 Hz), 8.34 (d, 1H, J=5 Hz), 7.87 (m, 1H), 7.41 (m, 1H), 6.84 (s, 1H), 6.67 (t, 2H, J=8 Hz), 6.51 (s, 1H), 5.04 (d, 2H, J=6 Hz), 3.82 (s, 2H).

EXAMPLE 45

N-{[5-(1H-pyrazol-5-yl)-1,3,4-thiadiazol-2-yl]methyl}-4-(2,4,6-trifluorobenzyl)-1H-pyrrole-2-carboxamide

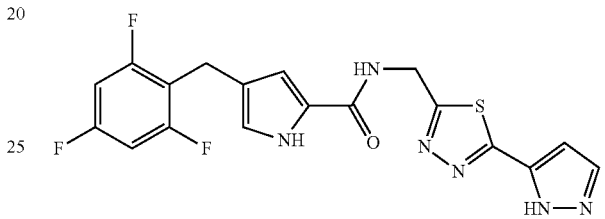

The title compound was prepared following the procedure described in example 32 employing intermediate 5 instead of intermediate 1.

$^1$H-NMR (d$_6$-DMSO, 500 MHz): δ 13.4 (s, 1H), 11.4 (s, 1H), 8.92 (t, 1H, J=6 Hz), 7.92 (s, 1H), 7.15 (t, 2H, J=8 Hz), 6.84 (s, 1H), 6.62 (s, 1H), 4.73 (d, 2H, J=6 Hz), 3.32 (s, 2H).

EXAMPLE 46

N-{[5-(3-methyl-1H-pyrazol-5-yl)-1,3,4-thiadiazol-2-yl]methyl}-4-(2,4,6-trifluorobenzyl)-1H-pyrrole-2-carboxamide

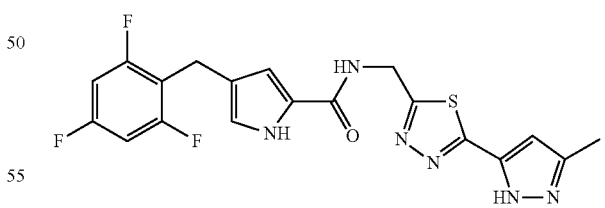

The title compound was prepared following the procedure described in example 20 employing intermediate 5 instead of intermediate 1.

$^1$H-NMR (d$_6$-DMSO, 500 MHz): δ 13.1 (s, 1H), 11.4 (s, 1H), 8.9 (t, 1H, J=6 Hz), 7.15 (t, 2H, J=8 Hz), 6.71 (s, 1H), 6.62 (s, 1H), 6.58 (s, 1H), 4.72 (d, 2H, J=6 Hz), 3.69 (s, 2H), 2.28 (s, 3H). LC/MS: m/z=433 (M+H).

Alternate Preparation of Example 32
Step 1. Friedel Crafts

Scheme:

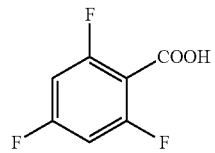

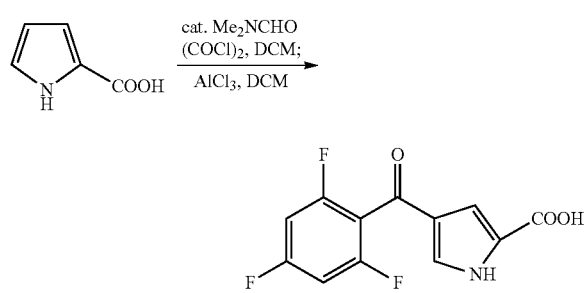

Procedure:

NOTE: This procedure was carried out in two batches and each was treated the same.

A 50 L multineck round-bottom flask in a steam pot and equipped with an overhead stirrer, thermocouple probe, and addition funnel with nitrogen inlet atop was charged with 2,4,6-trifluorobenzoic acid, dichloromethane, and DMF. The nitrogen inlet was vented to a NaOH scrubber. Oxalyl chloride was charged to the addition funnel and added over 15 min during which time the temperature dropped to 10° C. with gas evolution. The reaction was stirred for 1 hr, warming to 17° C. After three more hours @ rt a sample was checked by HPLC for completeness. The sample was quenched into methanol.

A 75 L multineck round-bottom flask in a steam pot and equipped with an overhead stirrer, thermocouple probe, and nitrogen inlet was charged with aluminum chloride slurried in dichloromethane. To this slurry was added the solution of acid chloride over 5 min with concomitant temperature rise from 17° C. to 22° C. The mixture was aged at rt for 45 min. Pyrrole-2-carboxylic acid was added in several portions over 40 min with vigorous gas evolution following each charge. The temperature rose to 23° C. After 30 min at rt a sample was taken and checked for completeness by HPLC. The reaction mixture was stirred for an additional 2 hrs before being packed in ice and topped with dry ice to cool it overnight. A 100 L multineck round-bottom flask in a steam pot and

Reagent table

| Reagent | MW | stoic | d | Amount | mole |
|---|---|---|---|---|---|
| 2,4,6-Trifluorobenzoic acid | 176.09 | 1.0 eq | — | 2.924 kg | 16.605 |
| Dichloromethane | — | 5 L/kg | 1.325 | 15 L | — |
| N,N-Dimethylformamide | 73.09 | 1 mol % | 0.944 | 15 mL | 0.194 |
| Oxalyl chloride | 126.93 | 1.04 eq | 1.455 | 1.515 L | 11.936 |
| Aluminum chloride | 133.34 | 2.85 eq | — | 6.3 kg | 47.248 |
| Dichloromethane | — | 5 L/kg | 1.325 | 15 L | — |
| 2-Pyrrole carboxylic acid | 111.10 | 1.02 eq | — | 1.89 kg | 17.012 |
| 1M HCl (quench) | — | 20 L/kg | — | 60 L | — |
| 1M HCl (rinse) | — | 2 × 2.8 L/kg | — | 2 × 8 L | — |
| Water (rinse) | — | 1 × 2.8 L/kg  2 × 1.4 L/kg | — | 8 L, 2 × 4 L | — |
| Methanol (rex) | — | 14 L/kg | — | 40 L | — |
| Water (antisolvent) | — | 7 L/kg | — | 20 L | — |
| 2:1 MeOH : water (rinse) | — | 1 L/kg  0.7 L/kg | — | 3.2 L | — |
| Acylated pyrrole acid | 269.18 | 1.0 eq | — | (4.470 kg) | 16.605 |
| 2,4,6-Trifluorobenzoic acid | 176.09 | 1.0 eq | — | 3.019 kg | 17.145 |
| Dichloromethane | — | 5 L/kg | 1.325 | 15 L | — |
| N,N-Dimethylformamide | 73.09 | 1 mol % | 0.944 | 151 mL | 0.194 |
| Oxalyl chloride | 126.93 | 1.01 eq | 1.455 | 1.52 L | 11.975 |
| Aluminum chloride | 133.34 | 2.71 eq | — | 6.2 kg | 46.498 |
| Dichloromethane | — | 5 L/kg | 1.325 | 15 L | — |
| 2-Pyrrole carboxylic acid | 111.10 | 1.00 eq | — | 1.89 kg | 17.012 |
| 1M HCl (quench) | — | 20 L/kg | — | 60 L | — |
| 1M HCl (rinse) | — | 2 × 3.3 L/kg | — | 2 × 10 L | — |
| Water (rinse) | — | 2 × 3.3 L/kg | — | 2 × 10 L | — |
| Methanol (rex) | — | 14 L/kg | — | 44 L | — |
| Water (anitisolvent) | — | 7 L/kg | — | 22 L | — |
| 2:1 MeOH : water (rinse) | — | 1.3, 0.7 L/kg | — | 4.2 L | — |
| Acylated pyrrole acid | 269.18 | 1.0 eq | — | (4.615 kg) | 17.145 | equipped with an overhead stirrer, thermocouple probe, and nitrogen inlet was charged with HCl and packed with ice to cool it overnight.

To the cooled HCl solution was added the reaction mixture over 1½ hrs with a temperature rise to 24° C. The resulting slurry was aged for 1 hr at rt and was then filtered. The cake was washed with more HCl followed by water.

The cake was dried in a nitrogen tent overnight. The damp cake was then dried in a vacuum oven at 55° C. with nitrogen sweep over the weekend. The resulting solid was a 100 L multineck round-bottom flask in a steam pot and equipped with an overhead stirrer, thermocouple probe, and addition funnel with nitrogen inlet atop was charged with the crude arylated pyrrole acid product and methanol. This slurry was heated to 48° C. to dissolve the product at which time it was allowed to cool. Upon reaching 30° C. water was added via the addition funnel over 1 hr.

The slurry was cooled to 5° C. and aged for 2 hrs. The slurry was then filtered at 5° C. and the cake was washed with cold (5° C.) methanol:water. The wet solid product was checked for regioisomer level by HPLC. The cake was dried in a nitrogen tent overnight before packaging.

NMR:
$^1$H (DMSO, 400 MHz) δ 12.92 (br. s, 1H), 12.70 (br. s, 1H), 7.58 (dd, 1H, J=3.4, 1.5 Hz), 7.31 (dd, 2H, J=9.4, 7.9 Hz), 7.04 (t, 1H, J=2.0 Hz).
$^{13}$C (DMSO, 100 MHz) □ 180.8, 162.8 (dt, $J_{CF}$=249.41, 15.72 Hz), 161.4, 159.2 (ddd, $J_{CF}$=248.60, 15.76, 11.15 Hz), 130.2, 125.9, 125.9, 114.7 (td, $J_{CF}$=18.75, 4.71 Hz), 114.3, 101.4 (td, $J_{CF}$=23.98, 3.01 Hz).
$^{19}$F (DMSO, 376 MHz) □ −105.26, −105.28, −105.29, −111.11, −111.13.
HRMS: [M−H]$^-$ C$_{12}$H$_2$O$_3$NF$_3^-$ calc'd, 268.0222. found, 268.0228; error: 2.2 ppm.

2,4,6-Trifluorobenzoic acid

NMR:
$^1$H (DMSO, 400 MHz) δ 13.89 (br. s, 1H), 7.27 (m, 2H).
$^{13}$C (DMSO, 100 MHz) δ 163.28 (dt, $J_{CF}$=250.9, 16.0 Hz), 161.5, 160.3 (ddd, $J_{CF}$=253.6, 15.8, 9.7 Hz), 109.0 (td, $J_{CF}$=19.5, 4.7 Hz), 101.5 (td, $J_{CF}$=26.8, 3.5 Hz).
$^{19}$F (DMSO, 376 MHz) δ −103.6, −103.6, −103.7, −108.3, −108.3.

Pyrrole-2-carboxylic acid

NMR:
$^1$H (DMSO, 400 MHz) δ 12.16 (br. s, 1H), 11.68 (br. s, 1H), 5.70 (m, 1H), 6.71 (m, 1H), 6.13 (m, 1H).
$^{13}$C (DMSO, 100 MHz) δ 161.9, 123.4, 122.9, 114.7, 109.3.

Step 2. Acyl Hydrazide Formation

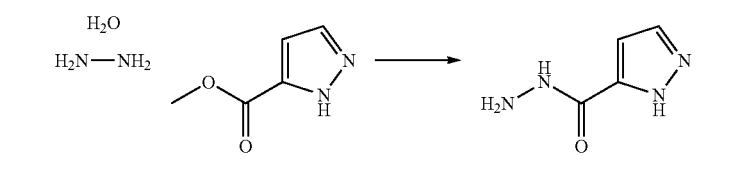

| | Structure | Reactant | Mol Wt | Eq | Moles (mmol) | Mass (g) | Vol (ml) | d (g/ml) | % Wt (%) |
|---|---|---|---|---|---|---|---|---|---|
| 1 | | | 126.11 | 1.00 | 1110 | 140 | | | |
| 2 | H$_2$O H$_2$N—NH$_2$ | HYDRAZINE HYDRATE | 50.06 | 1.4 | 1554 | 97 | 94 | 1.03 | 80 |

| Product | Formula | Actual Mass (g) | Yield (%) | Parent Wt | Theo Mol (mmol) | Theo Mass (g) |
|---|---|---|---|---|---|---|
| 1 | C4H6N4O | 120 | 86 | 126.12 | 1110 | 140 |

Experimental:

To the reaction vessel was charged the methyl ester (140 g, 1110 mmol), HYDRAZINE HYDRATE (94 ml, 1554 mmol) and Methanol (700 ml) then heated to reflux.

LC Profile: 45 min: 72% conversion; 1.25 hrs 85% conversion

The reaction was aged for an additional 2.5 hours, then stir at r.t overnight after which LC analysis shows reaction was complete. The resulting slurry was cooled 3° C., the solids filtered and washed with 200 ml water then dried under nitrogen stream to give 120 g (86% yield) of the acyl hydrazide.

Step 3. Chloroacetylation

Experimental:

Reactant 1 (100 g, 793 mmol) was suspended in ethyl acetate (1000 ml) in a 3 L 3-necked RBF with overhead stirring and the treated with potassium bicarbonate (600 ml, 1800 mmol). Reaction was then cooled to 5° C., after which chloroacetyl chloride (76 ml, 952 mmol) was added over 7 minutes. Exotherm to 16° C. was observed. LC assay after 15 min shows reaction complete. Add 100 ml 6N HCl, then add another 15 ml 12N HCl to bring pH to 4.6. Filter off solids, wash cake with ea 150 ml of cold water and dry overnight under a nitrogen stream to give 143.7 g (89%) of the desired product.

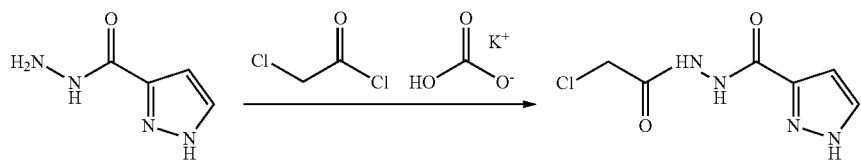

| | Structure | Mol Wt | Eq | Moles (mmol) | Mass (g) | Vol (ml) | M (M) | d (g/ml) |
|---|---|---|---|---|---|---|---|---|
| 1 | 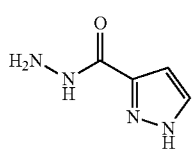 | 126.12 | 1.00 | 793 | 100 | | | |
| 2 | 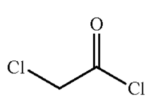 | 112.94 | 1.2 | 952 | 107 | 76 | | 1.418 |
| 3 | 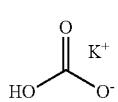 | 100.12 | 2.27 | 1800 | | 600 | 3 | |

| Product | Formula | Actual Mass (g) | Yield (%) | Parent Wt | Theo Mass (g) |
|---|---|---|---|---|---|
| 1 | C6H7ClN4O2 | 143.7 | 89 | 202.60 | 161 |

Step 4. Cyclization

| | Structure | Reactant | Formula | Mol Wt | Eq | Moles (mmol) | Mass (g) |
|---|---|---|---|---|---|---|---|
| 1 | 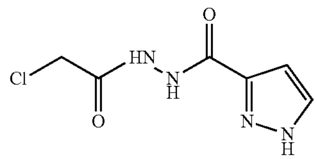 [SMILES: O=C(CCl)NNC(=O)c1cc[nH]n1] | | C6H7ClN4O2 | 202.60 | 1.00 | 370 | 75 |
| 2 | 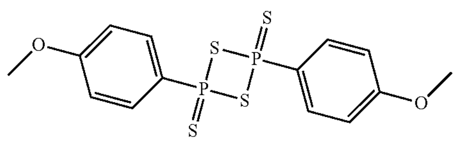 | LAWESSON'S REAGENT | C14 H14 O2 P2 S4 | 404.47 | 1.00 | 370 | 150 |

| Product | Formula | Actual Mass (g) | Yield (%) | Parent Wt | Theo Mol (mmol) | Theo Mass (g) | Mol Wt |
|---|---|---|---|---|---|---|---|
| 1 | C6H5ClN4S | 41. | 55.2 | 200.65 | 370 | 74.3 | 200.65 |

Experimental:

Suspend Reactant 1 (75 g, 370 mmol) and LAWESSON'S REAGENT (150 g, 370 mmol) in THF (1500 ml) then heat to reflux under nitrogen for 2.5 hrs. The reaction was then cooled to r.t. and concentrated. The resulting residue was dissolved in 250 ml EtOAc, treated with 300 g silica gel then filtered. The cake was washed with 3×500 mL EtOAc. The 1st fraction was passed through a silica plug again and the rich cuts were concentrated and redissolved in DCM; chromatographed on silica gel, 1.5 kg column; elute with EtOAc/heptane 50-60%. Strip rich cuts to give 41 g solid (55.2%).

Step 5. Sodium Azide Displacement

| | Structure | Reactant | Mol Wt | Eq | Moles (mmol) | Mass (g) |
|---|---|---|---|---|---|---|
| 1 | 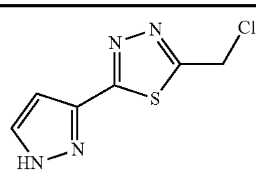 | | 200.65 | 1.00 | 189 | 38 |
| 2 | 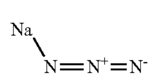 | | 65.01 | 1.05 | 199 | 12.93 |

| Product | Formula | Actual Mass (g) | Yield (%) | Parent Wt | Theo Mol (mmol) | Theo Mass (g) |
|---|---|---|---|---|---|---|
| 1 | C6H5N7S | 36.3 | 92 | 207.22 | 189 | 39.2 |

Experimental:

Dissolve Reactant 1 (38 g, 189 mmol) in DMF (160 ml) at Lt. Add sodium azide (12.93 g, 199 mmol); stir at ambient temp. Mixture turned orange, a solid began to precipitate after a few minutes.

After the reaction was allowed to stir over weekend, LC assay shows reaction completed. 250 ml water (mildly exothermic) was added resulting to a homogeneous solution, then solids began crystallizing out. The slurry was cooled to 5° C., filtered, washed with 2×100 mL cold water and dried to give 36.6 g (92%) product.

Step 6. Azide Reduction

| | Structure | Reactant | Mol Wt | Eq | Moles (mmol) | Mass (g) | Vol (ml) | M (M) |
|---|---|---|---|---|---|---|---|---|
| 1 | 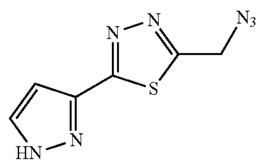 [SMILES: [N-]=[N+]=NCc1nnc(-c2cc[nH]n2)s1] | | 207.22 | 1.00 | 154 | 32.0 | | |
| 2 | 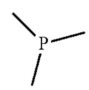 | TRIMETHYL-PHOSPHINE 1.0 M in THF | 76.08 | 1.1 | 170 | | 170 | 1.0 |
| 3 | H$_2$O | WATER | 18.02 | 2.88 | 445 | 8.01 | | |

Experimental:

Suspend Reactant 1 (32.0 g, 154 mmol) in THF (160 ml); add WATER (8.01 g, 445 mmol). Add TRIMETHYLPHOSPHINE 1.0M in THF (170 ml, 170 mmol), dropwise, over one hour. Assay after two hours shows no SM remain. The solution was concentrated and the resulting residue was treated with 160 mL 2N HCl and stirred at RT overnight.

The solution was then basified with 60 mL 5N NaOH. Add 160 mL 1N NaHCO3 and used directly in the subsequent final coupling reaction.

Step 7a. Activation

| | Structure | Reactant | Mol Wt | Eq | Moles (mmol) | Mass (g) | Vol (ml) | d (g/ml) |
|---|---|---|---|---|---|---|---|---|
| 1 | 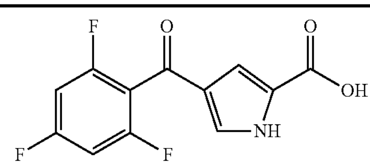 | | 269.18 | 1.00 | 154 | 41.5 | | |
| 2 | 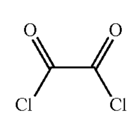 | OXALYL CHLORIDE | 126.93 | 1.05 | 162 | 20.52 | 14.15 | 1.45 |

Experimental:

Dissolve Reactant 1 (41.5 g, 154 mmol) in THF (415 ml); add 0.25 mL DMF, then add OXALYL CHLORIDE (14.15 ml, 162 mmol). The solution was stirred at RT for 1 hour then concentrated. The resulting residue was diluted with 200 mL 2-MeTHF and used directly in final coupling step.

Step 7b. Final Coupling

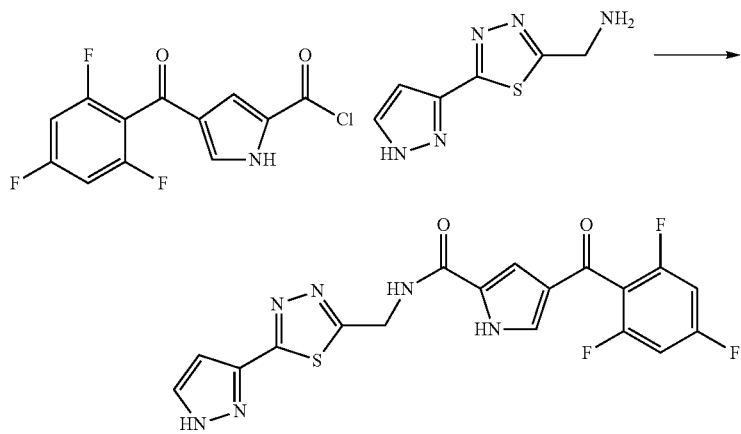

| | | | Mol | | Moles | Mass |
|---|---|---|---|---|---|---|
| | Structure | Reactant | Wt | Eq | (mmol) | (g) |
| 1 | | | 287.62 | 1.00 | 154 | 44.3 |
| 2 | | | 181.22 | 1.00 | 154 | 27.9 |

| | | Actual Mass | Actual Mol | Parent | Theo Mass | Mol |
|---|---|---|---|---|---|---|
| Product | Formula | (g) | (mmol) | Wt | (g) | Wt |
| 1 | C18H11F3N6O2S | 44.65 | 103 | 432.38 | 66.6 | 432.38 |

Experimental:

The acid chloride and amine crude solutions were combined and stirred at RT for 2 hrs. After reaction is complete (by LC analysis), the solution was concentrated to remove organic solvents and the resulting aqueous slurry was filtered, the solids washed with water (100 mL, 150 mL), then with 150 ml acetonitrile and sucked dry to give 72 g pale green solid.

Recrystallization

Charge 71.8 g solid to a 22 L RBF and added 7.0 L acetonitrile and 3.5 L water then heated to 77° C. Filter hot mixture through a sintered funnel to remove insolubles. (Filtrate slightly turbid). Pump filtrate (61° C.) into a clean 22 L RBF through a 5 μ line filter to give a clear, yellow solution. Allow to cool slowly to 30° C., and then chill to 5° C. Filter off solids, wash cake with 250 mL 2/1 acetonitrile/water, vacuum dry overnight to give 44.65 g (67% yield over 2 steps and recrystallization) of final product.

What is claimed is:

1. A compound represented by chemical formula (I)

[Chemical structure of formula (I): Ar¹-L connected to a pyrrole ring with NH, bearing a C(O)-NH-CH₂-Ar² group]

or a pharmaceutically acceptable salt thereof, wherein:

L is selected from the group consisting of:
(a) —C(O)—,
(b) —CH(OH)—
(c) —CH(NR$^3$R$^4$)—
(d) —C(=NOR$^3$)—,
(e) —CH$_2$—, and
(f) —S(O)$_n$—, wherein n is 0, 1 or 2;

Ar$^1$ is an optionally mono, di- or tri-substituted phenyl or heteroaromatic ring of 6 atoms, wherein the heteroaromatic ring may contain 1, 2 or 3 heteroatoms selected from N, S and O, wherein the substituents are independently selected from the group consisting of:
(a) halo,
(b) —C$_{1-4}$alkyl,
(c) —O—C$_{1-4}$alkyl,
(d) —CF$_3$,
(e) —NH$_2$,
(f) —NH—CH$_3$,
(g) —CN,
(h) —C(O)NH$_2$, and
(i) —S(O)$_n$—CH$_3$;

Ar$^2$ is an optionally substituted thiadiazole or oxadiazole ring wherein thesubstituent is a phenyl or a 5 or 6 membered mono-cyclic heteroaromatic or heterocyclic ring, or a bicyclic heteroaromatic or heterocyclic ring of 9 or 10 atoms, said heteroaromatic or heterocyclic ring containing 1, 2 or 3 hetero atoms selected from the group consisting of S, O and N, where in said phenyl, heteroaromatic or heterocyclic ring is optionally mono or di-substituted with substituents independently selected from the group consisting of:
(a) halo,
(b) —C$_{1-6}$alkyl, optionally substituted with 1 to 4 fluorine atoms
(c) —O—C$_{1-6}$alkyl,
(d) —CF$_3$,
(e) —NH$_2$,
(f) —NH—CH$_3$,
(g) —NH—CH$_2$CF$_3$,
(h) —C(O)-morpholinyl,
(i) —C(O)—NR$^1$R$^2$,
(j) —C(O)OH,
(k) —CN,
(l) oxo, and
(m) C$_{3-6}$cycloalkyl;

R$^1$, R$^2$, R$^3$ and R$^4$ are independently selected from the group consisting of
(a) hydrogen, and
(b) C$_{1-4}$alkyl, or R$^1$ and R$^2$ or R$^3$ and R$^4$ may be joined together to form a 5 or 6 membered saturated ring, said ring optionally containing a heteroatom selected from S, N and O.

2. The compound according to claim 1, wherein
L is selected from the group consisting of:
(a) —C(O)—, and
(b) —CH$_2$—.

3. The compound according to claim 2, wherein
L is —C(O)—.

4. The compound according to claim 1, wherein
Ar$^1$ is an optionally mono, di- or tri-substituted phenyl or heteroaromatic ring of 6 atoms, wherein the heteroaromatic ring may contain 1, 2 or 3 heteroatoms selected from N, S and O, wherein the substituents are independently selected from the group consisting of:
(a) halo,
(b) —C$_{1-4}$alkyl, and
(c) —O—C$_{1-4}$alkyl.

5. The compound according to claim 4, wherein
Ar$^1$ is an optionally mono, di- or tri-substituted phenyl or pyridyl, wherein the substituents are independently selected from the group consisting of
(a) fluoro,
(b) chloro, and
(c) —CH$_3$.

6. The compound according to claim 5, wherein
Ar$^1$ is an optionally mono, di- or tri-substituted phenyl, wherein the substituents are independently selected from the group consisting of
(a) fluoro,
(b) chloro, and
(c) —CH$_3$.

7. The compound according to claim 1 wherein
Ar$^2$ is an optionally substituted thiadiazolyl.

8. The compound according to claim 7 wherein
the substituent is phenyl or a 5 or 6 membered mono-cyclic heteroaromatic or heterocyclic ring, or a 9 or 10 atom bicyclic heteroaromatic or heterocyclic ring, said hetero aromatic or heterocyclic ring containing 1, 2 or 3 hetero atoms selected from the group consisting of S, O and N, where in said phenyl, heteroaromatic or heterocyclic ring is optionally mono or di-substituted with substituents independently selected from the group consisting of:
(a) halo,
(b) —C$_{1-6}$alkyl, optionally substituted with CF$_3$,
(c) —O—C$_{1-4}$alkyl,
(d) —CF$_3$, and
(e) C$_{3-6}$cycloalkyl.

9. The compound according to claim 8 wherein
the substituent is phenyl or a 5 or 6 membered mono-cyclic heteroaromatic or heterocyclic ring, said hetero aromatic or heterocyclic ring containing 1, 2 or 3 hetero atoms selected from the group consisting of S, O and N, where in said phenyl, heteroaromatic or heterocyclic ring is optionally mono or di-substituted with substituents independently selected from the group consisting of:
(a) halo,
(b) —C$_{1-6}$alkyl, optionally substituted with CF$_3$,
(c) —O—C$_{1-4}$alkyl,
(d) —CF$_3$, and
(e) C$_{3-6}$cycloalkyl.

10. The compound according to claim 1 wherein
R$^1$, R$^2$, R$^3$ and R$^4$ are independently selected from the group consisting of
(a) hydrogen, and
(b) methyl.

11. A compound according to claim 1 of Formula I (I)

or a pharmaceutically acceptable salt thereof, wherein:
L is —C(O)—;
Ar¹ is an optionally a mono, di- or tri-substituted phenyl, wherein the phenyl is substituted with substituents independently selected from the group consisting of:
(a) F,
(b) Cl,
(c) —$C_{1-4}$alkyl, and
(d) —O—$C_{1-4}$alkyl;
Ar² is optionally substituted thiadiazolyl, and
the substituent is phenyl or a 5 or 6 membered mono-cyclic heteroaromatic or heterocyclic ring, said hetero aromatic or heterocyclic ring containing 1, 2 or 3 hetero atoms selected from the group consisting of S, O and N, where in said phenyl, heteroaromatic or heterocyclic ring is optionally mono or di-substituted with substituents independently selected from the group consisting of:
(a) halo,
(b) —$C_{1-4}$alkyl,
(c) —O—$C_{1-4}$alkyl,
(d) —$CF_3$,
(e) $C_{3-6}$cycloalkyl.

12. A compound according to claim 1 having the following structure or a pharmaceutically acceptable salt thereof, wherein:
Ar² is optionally substituted thiadiazolyl, wherein the substituent is phenyl or a 5 or 6 membered mono-cyclic heteroaromatic or heterocyclic ring, said hetero aromatic or heterocyclic ring containing 1, 2 or 3 hetero atoms selected from the group consisting of S, O and N, where in said phenyl, heteroaromatic or heterocyclic ring is optionally mono or di-substituted with substituents independently selected from the group consisting of:
(a) halo,
(b) —$C_{2-6}$alkyl,
(c) —O—$C_{1-4}$alkyl, and
(d) —$CF_3$.

13. The compound according to claim 1, selected from the group consisting of:

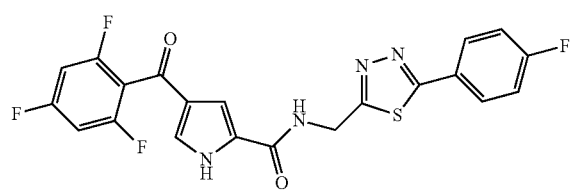
8
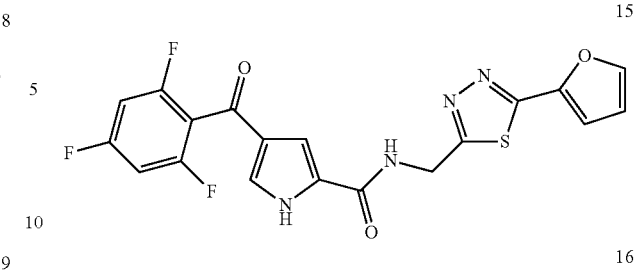
15
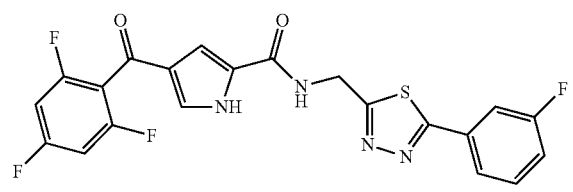
9
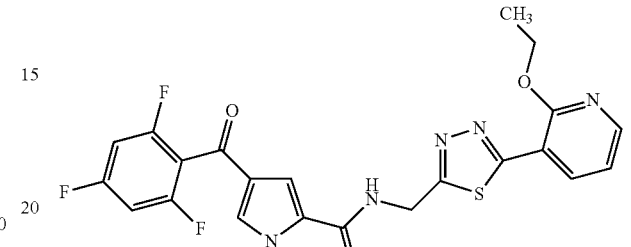
16
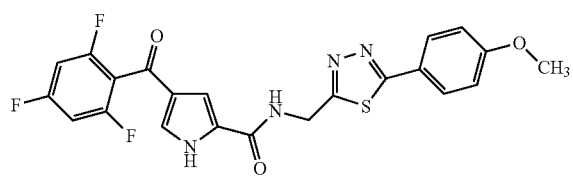
10
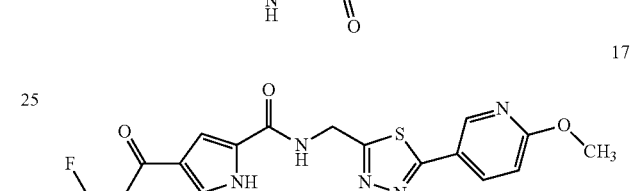
17
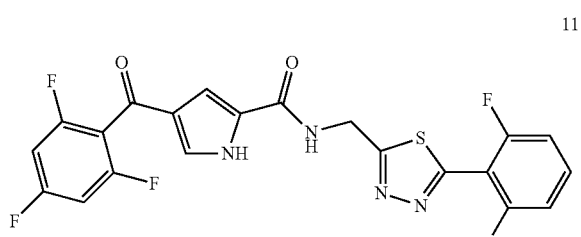
11
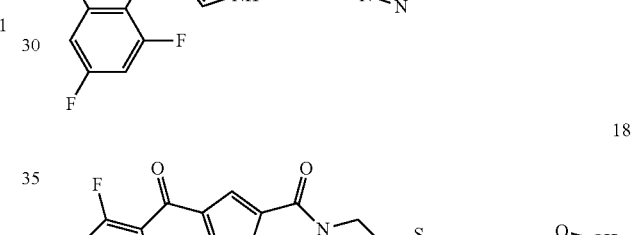
18
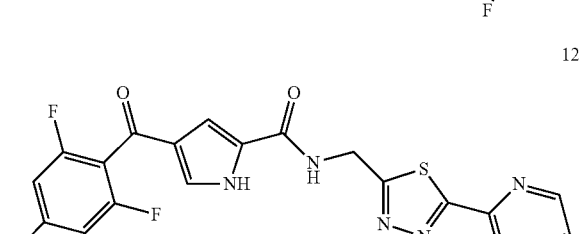
12
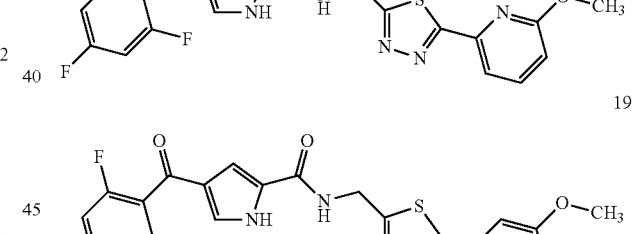
19
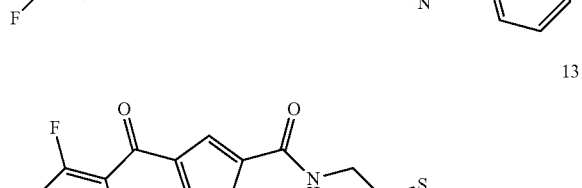
13
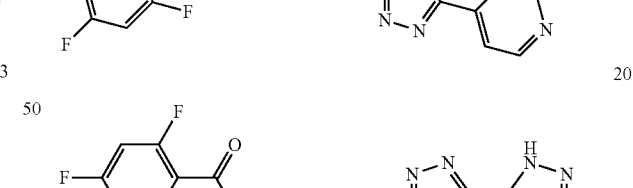
20
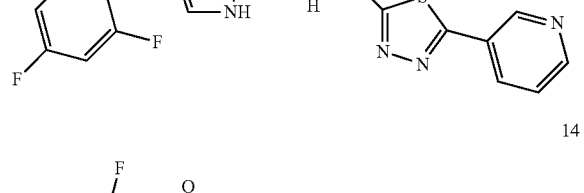
14
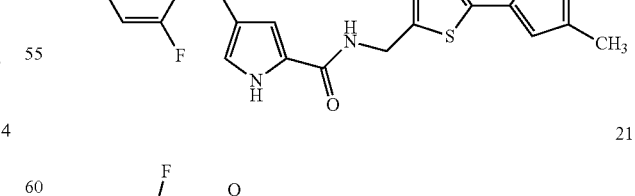
21
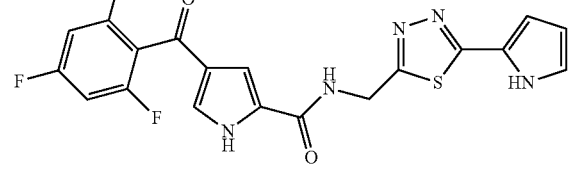
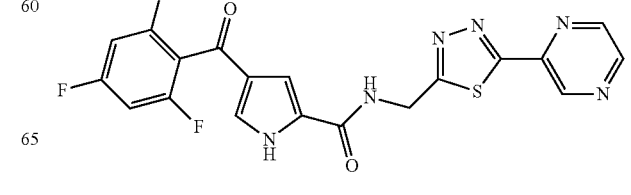

34
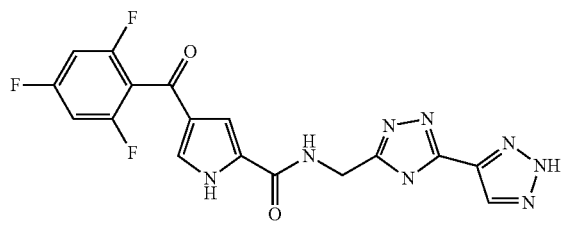
35
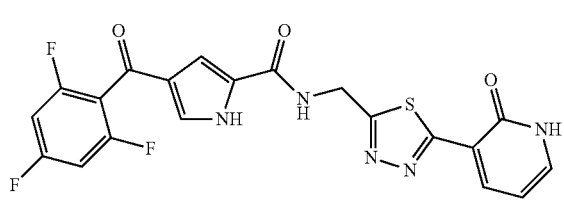
36
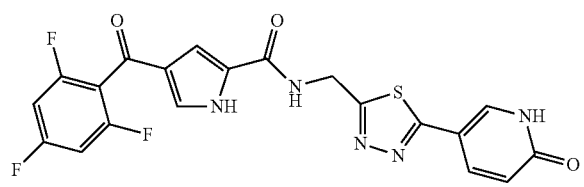
37
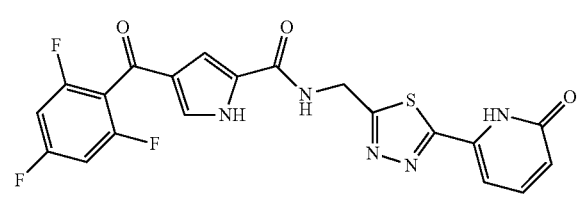
38
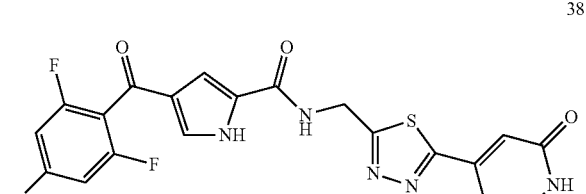
39
40
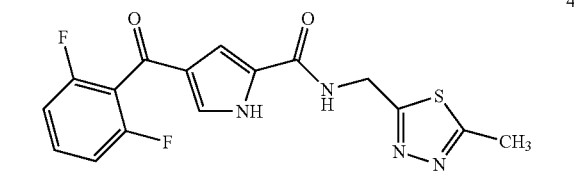
41
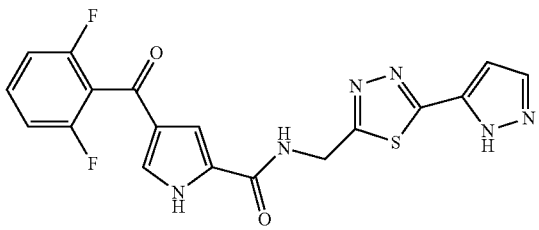
42
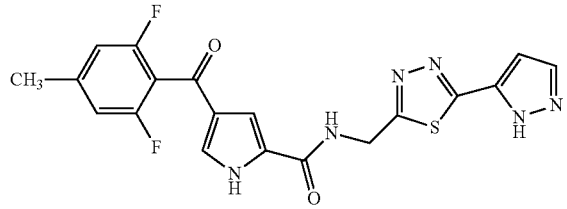
43
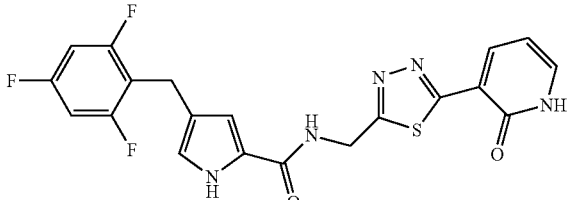
44
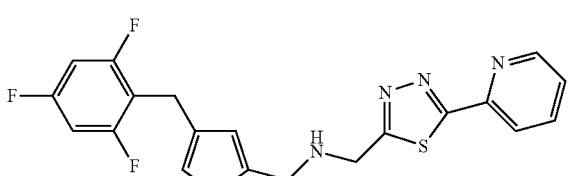
45
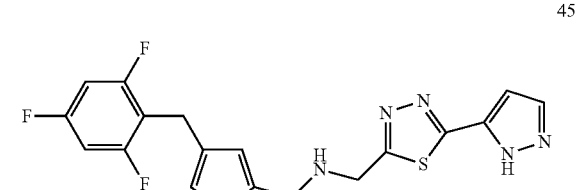
46
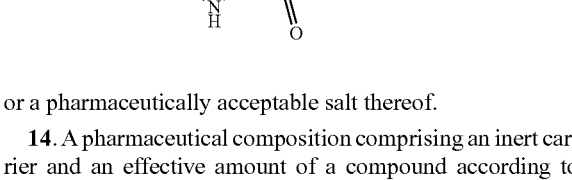
or a pharmaceutically acceptable salt thereof.
14. A pharmaceutical composition comprising an inert carrier and an effective amount of a compound according to claim 1.

15. A compound having the following structure
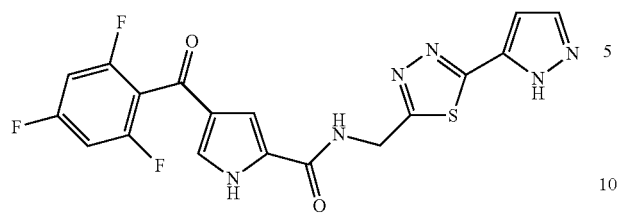
or a pharmaceutically acceptable salt thereof.
16. A pharmaceutical composition comprising an inert carrier and an effective amount of the compound of claim 15.
* * * * *